US010444385B1

(12) United States Patent
Newman

(10) Patent No.: US 10,444,385 B1
(45) Date of Patent: Oct. 15, 2019

(54) SHIELDLESS DETECTOR WITH ONE-DIMENSIONAL DIRECTIONALITY

(71) Applicant: David Edward Newman, Poway, CA (US)

(72) Inventor: David Edward Newman, Poway, CA (US)

( * ) Notice: Subject to any disclaimer, the term of this patent is extended or adjusted under 35 U.S.C. 154(b) by 0 days.

(21) Appl. No.: 16/431,687

(22) Filed: Jun. 4, 2019

Related U.S. Application Data

(60) Provisional application No. 62/713,245, filed on Aug. 1, 2018.

(51) Int. Cl.
*G01T 1/20* (2006.01)
*G01T 3/06* (2006.01)
*G01T 3/08* (2006.01)
*G01N 23/09* (2018.01)
*G01T 1/29* (2006.01)
*G01N 23/04* (2018.01)

(52) U.S. Cl.
CPC ............... *G01T 3/06* (2013.01); *G01N 23/04* (2013.01); *G01N 23/09* (2013.01); *G01T 1/20* (2013.01); *G01T 1/2907* (2013.01); *G01T 3/08* (2013.01)

(58) Field of Classification Search
CPC ......... G01N 2223/626; G01N 2030/77; G01N 23/306; G01N 23/095; G01N 23/223; G01D 5/50
See application file for complete search history.

(56) References Cited

U.S. PATENT DOCUMENTS

| 3,047,721 | A | 7/1962 | Folsom |
| 3,581,090 | A | 5/1971 | Brown |
| 5,354,084 | A | 9/1994 | Byrd |
| 5,665,970 | A | 9/1997 | Kronenberg |
| 5,880,469 | A | 3/1999 | Miller |
| 6,433,335 | B1 | 8/2002 | Kronenberg |
| 6,639,210 | B2 | 10/2003 | Odom |
| 7,521,686 | B2 | 4/2009 | Stuenkel |
| 7,745,800 | B1 | 6/2010 | McGinnis |
| 7,952,079 | B2 | 5/2011 | Neustadter |
| 7,994,482 | B2 | 8/2011 | Frank |
| 8,030,617 | B2 | 10/2011 | Enghardt |
| 8,067,742 | B2 | 11/2011 | Winso |
| 8,198,600 | B2 | 6/2012 | Neustadter |

(Continued)

*Primary Examiner* — David P Porta
*Assistant Examiner* — Mamadou Faye

(57) ABSTRACT

A system of particle detectors can determine the location of a source without rotations or iterations. Embodiments of the system may include a middle detector flanked by two side detector panels, without shields or collimators. The middle detector may be positioned toward the front and orthogonal to the side detectors. By comparing a ratio of the detector data to a predetermined angular correlation function, the system can determine both the sign and magnitude of the source angle in real-time. Embodiments of the system can rapidly and automatically localize sources including industrial, medical, and other benign sources as well as nuclear and radiological weapons materials, whether in vehicles or cargo containers, and can provide improved sensitivity in walk-through personnel portal applications, enable enhanced detection of hidden weapons by a mobile area scanner, and enable a hand-held survey meter that indicates the radiation level as well as the location of the source of radiation.

20 Claims, 20 Drawing Sheets

(56) References Cited

U.S. PATENT DOCUMENTS

| | | |
|---|---|---|
| 8,242,456 B1 | 8/2012 | Hecht |
| 8,247,776 B2 | 8/2012 | Peng |
| 8,319,188 B2 | 11/2012 | Ramsden |
| 8,866,100 B1 | 10/2014 | Marleau |
| 8,930,165 B2 | 1/2015 | Vilim |
| 9,012,855 B2 | 4/2015 | Speller |
| 9,575,189 B2 | 2/2017 | Groves |
| 2003/0165211 A1 | 7/2003 | Grodzins |
| 2005/0121618 A1 | 6/2005 | Fowler |
| 2008/0048123 A1 | 2/2008 | Larsson |
| 2010/0006769 A1* | 1/2010 | Kraft ............... G01T 1/167 250/370.11 |
| 2013/0256538 A1 | 10/2013 | Vogtmeier |
| 2014/0374606 A1 | 12/2014 | Gendotti |
| 2016/0154140 A1* | 6/2016 | Hedin ............... G01V 5/025 250/253 |
| 2017/0261623 A1 | 9/2017 | Florido |

\* cited by examiner

SHIELDLESS DETECTOR WITH ONE-DIMENSIONAL DIRECTIONALITY

CROSS REFERENCE TO RELATED APPLICATIONS

This application claims the benefit of U.S. Provisional Patent Application No. 62/713,245 entitled "Directional Radiation Monitor with Middle Detector" and filed on Aug. 1, 2018, the entire disclosure of which is incorporated by reference as part of the specification of this application.

FIELD OF THE INVENTION

The present invention relates generally to radioactive source detection. More particularly, the present invention is directed in one exemplary aspect to a directional radiation detection system that determines an angle of the radiation source, relative to the system, including the sign and magnitude of the source angle.

BACKGROUND

Radioactive sources are increasingly prevalent in modern society. Radioactive sources provide many benefits as well as risks such as accidental exposure, loss or pilferage of the sources, and clandestine transport of nuclear weapon materials, among other risks. Nations must be able to detect radioactive sources and to determine their locations, despite ubiquitous background radiation from cosmic rays and benign environmental sources. In addition, radioactive material from a spill or accident must be localized for removal or avoidance. Search personnel are subject to continuous exposure to radiation while attempting to localize a lost or hidden source. Determining the direction toward a source would greatly speed up the search process, thereby rapidly localizing sources that may otherwise be missed, and minimizing the dose absorbed by personnel.

What is needed is a compact, rugged, light-weight, efficient detector that indicates the specific direction of a source of gamma rays or neutrons, without extensive searching or iteration. Preferably the new detector would have sufficient sensitivity to detect both large and small sources, with sufficient angular precision to localize the source among clutter and obfuscation, rapidly, with high efficiency, and at low cost.

SUMMARY

A system for detection and localization of a radioactive source includes two side detectors, separated by a predetermined distance and oriented parallel to a centrally positioned aiming plane, wherein each side detector is configured to emit signals upon detecting particles from the source, and to block at least 50% of the particles orthogonally incident thereon; a middle detector positioned at least partially between the side detectors, wherein the middle detector is positioned closer to the front of the system than the back of the system and configured to emit signals upon detecting particles from the source; and a processor configured to calculate, based at least in part upon the signals, the angle of the source location relative to the aiming plane.

These and other embodiments are described in further detail with reference to the figures and accompanying detailed description as provided below.

DETAILED DESCRIPTION OF INVENTION

Figure 1:
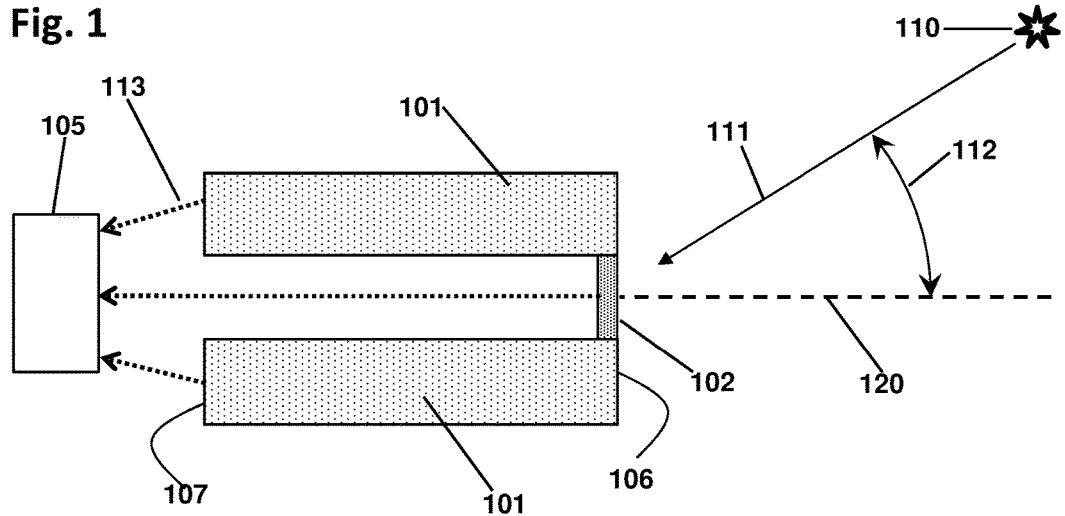
FIG. 1 is a sketch in cross-section of an exemplary system according to the disclosure comprising two side detectors and a middle detector according to some embodiments.

In the following description, reference is made to the accompanying drawings in which it is shown by way of illustration specific embodiments in which the invention can be practiced. Not all of the described components are necessarily drawn to scale in order to emphasize certain features and to better facilitate the reader's conception of the disclosed embodiments. It is to be understood that other embodiments can be used and structural changes can be made without departing from the scope of the embodiments of disclosed herein.

Disclosed herein are systems and methods for detecting and localizing radioactive sources such as radioactive material for medical or analytical purposes, nuclear and radiological weapons and their radioactive components, radioactive items following a spill or accident, and other radiation sources that are to be located. In some embodiments, a directional radiation detection system ("the system") can be configured to detect gamma rays or neutrons (the "particles") from a radioactive source, and to determine the direction of the source, relative to the system, in one dimension. Embodiments of the system can determine both the sign and magnitude of the source angle, based deterministically on particle data acquired at a single orientation of the system, with high detection efficiency and superior angular resolution. Examples are presented for detecting gamma rays and/or neutrons, but the principles disclosed herein are readily applicable to other particle types. In applications involving detection of radioactive materials, the ability to rapidly determine the source direction is an enabling improvement.

In some embodiments, the system may include two spaced-apart slab-shaped "side" detectors positioned facing each other and parallel to an "aiming plane" that runs centrally between the side detectors from the back to the front of the system, a third detector (the "middle detector") positioned at least partially between the side detectors, and an electronic processor. The side detectors may be separated by a predetermined distance, such as the width of the middle detector for example. In some embodiments, the distance between the middle detector and each side detector may be made as thin as practical, such as less than 1 mm, for optimal angular resolution. The middle detector may be slab-shaped and oriented perpendicular to the aiming plane, with its smallest dimension being parallel to the back-to-front direction. Alternatively, the middle detector may have a square cross-sectional shape or other shape and orientation. The middle detector may be positioned in various locations relative to the front of the side detectors, for example being recessed within the side detectors, or protruding frontwardly beyond the side detectors, or being flush (frontwardly coplanar) with the front of the side detectors. The side detectors and the middle detector (collectively the "detectors") may be configured to detect the particles, or their secondaries, and responsively emit distinct signals. Secondary particles ("secondaries") are particles generated by interactions of the incident particle, such as Compton electrons or photoelectrons from gamma ray interactions, or alpha particles or triton particles from neutron capture events, or recoil protons from neutron scattering events. In some embodiments, the side detectors may be thick enough to block a fraction of the orthogonally-incident particles, such as 10% or 50% or 90% of the particles, and thereby prevent the particles from detectably passing through into the other side detector. A detector "blocks" a fraction of the particles if the detector is thick enough to prevent the fraction of the particles, and their secondaries, from delivering a detectable amount of energy through the detector. A "detectable" amount of energy is an amount of energy at least equal to a predetermined threshold such as a discriminator setting. For example, a side detector of BGO scintillator 2.5 cm thick would block about 52% of orthogonally incident 1 MeV gamma rays from detectably reaching the other side detector, assuming that the other side detector has a 100 keV detection threshold. In some embodiments, the system may include no passive shields or collimators or other particle-blocking material (other than necessary detector wrapping and mounting brackets and the like, which are considered part of the respective detectors and are ignored herein). A shield or collimator is "passive" if it generates no signals, in contrast to an "active" collimator formed by detectors. In some embodiments, a shield "slug" may be positioned behind the middle detector.

The "signals" may include light pulses or electronic pulses or accumulated charge or counting rates or electrical voltages or currents or other detection data related to interactions of the particles, or their secondaries, in the detectors. Signals are "distinct" if they can be uniquely associated with a particular detector, thereby indicating which of the detectors detected each particle. For example, two electrical pulses on separate cables or conductors are distinct, two electronic pulses on the same conductor but with detectably different pulse shapes are distinct, two light pulses on separate light guides are distinct, and two light pulses having detectably different wavelengths are distinct, since in each case the signals can be analyzed and tallied separately. The processor may be configured to analyze the signals and to calculate the source angle based at least in part on the signals, wherein the "source angle" is the angle between the aiming plane and a line from the center of the system to the source location. For each detector, the processor may determine a "counting rate", equal to the number of particle detections in each detector within a particular time interval. The "midplane" is a centrally positioned plane, orthogonal to the side detectors, orthogonal to the aiming plane, orthogonal to the middle detector, and parallel to the back-to-front direction of the system. The "thickness" of a slab is its smallest dimension; the "length" of a slab is its longest dimension; the "width" of a slab is its intermediate dimension. The "lateral" direction is perpendicular to the aiming plane, and the "longitudinal" direction is the back-to-front direction. HDPE is high-density polyethylene. PMMA is polymethylmethacrylate. PVT is polyvinyltoluene. PSD means pulse-shape discrimination.

In some embodiments, the angular sensitivity of the middle detector may be determined by its shape, its orientation relative to the side detectors, and the partial blocking effects of the side detectors. The angular sensitivity of the side detectors may be determined by their shape, their orientation, and the partial blocking effect of the opposite side detector. The signal contrast between the side detectors may be determined by the ability of each side detector to prevent particles from crossing through and being detected in the opposite side detector, and therefore in some embodiments the side detectors may be thick enough to prevent most particles from passing through. The side detectors may have oppositely directed, antisymmetric angular sensitivities, while the middle detector may have a symmetrical angular sensitivity, relative to the aiming plane. An angular correlation function may be prepared to calculate the source angle by exploiting these different angular sensitivities. The angular correlation function may relate the source angle to a formula or analysis of the detection data of each detector. By this means, some embodiments of the system can determine the sign and magnitude of the source angle from data acquired at a single orientation.

FIG. 1 is a cross-section sketch of an exemplary embodiment of the system including two side detectors 101 (shown in light stipple), a middle detector 102 (dark stipple), and a processor 105. The system is facing to the right in this view and in all the figures unless otherwise noted. Also shown is the aiming plane 120 as a dashed line, since it is viewed edge-on in this cross-section view. The front of the system is indicated as 106, and the back is 107. The midplane is not shown because it lies in the plane of the paper. A source 110 is indicated by a star, and a particle trajectory 111 as an arrow. The source angle 112 is indicated as an arc. The side detectors 101 are parallel to the aiming plane 120. The middle detector 102 is closer to the front 106 than the back 107. In this case, the middle detector 102 is slab-shaped and is oriented perpendicular to the aiming plane 120, with its thickness parallel to the back-to-front direction. Signals 113, depicted as dotted arrows, flow from each detector 101-102 to the processor 105 for analysis. The processor 105 may include digital electronics, and optionally analog electronics, configured to calculate the source angle 112 from the signals 113 using a predetermined angular correlation function. As shown, the embodiment includes no passive shields or collimators.

The particle 111 may be a neutral particle such as a gamma ray or a neutron, or it may be a charged particle such as an electron or a proton. The detectors 101-102 may be suitable for detecting the particle 111 or its secondaries, such as scintillators, semiconductor detectors, and gaseous ionization detectors. Scintillators include organic types such as stilbene or polyvinyltoluene based scintillators of which many varieties are available, or inorganic types such as NaI, CsI, BGO, LYSO and many others, typically viewed by light sensors such as photomultiplier tubes, photodiodes, or microchannel plate sensors. Semiconductor detectors include n-type or p-type reverse-biased junctions, typically amplified by pulse amplifiers and other electronics. Gaseous ionization detectors include Geiger, proportional, and other types of tubes and chambers in which ionization charges in a gas are collected electrostatically, optionally amplified by avalanche, and linearly amplified by further electronics. In some embodiments, the sensor may be included in the associated detector, such as a semiconductor detector with an amplifier built-in. In other embodiments, the sensor may be included in the processor 105 or other electronics connected to the detector.

The detectors 101-102 may be configured to detect gamma rays. For example, the side detectors 101 may include low-cost plastic scintillator material or higher-performance inorganic scintillator such as $CaF_2$ or LYSO. The middle detector 102, being much smaller typically, may be made from a high-density scintillator such as $CdWO_4$ or BGO. Alternatively, all three detectors 101-102 may include the same material such as NaI(Tl) or CsI(Eu). Alternatively, the detectors 101-102 may include semiconductors such as reverse-biased planar diodes, or they may include gaseous ionization tubes or chambers configured to detect gamma-generated electrons by ionization of the gas, such as Geiger or proportional tubes.

The detectors 101-102 may be configured to detect neutrons. For example, the detectors 101-102 may include neutron-specific gamma-blind scintillators such as ZnS coupled with a lithium or boron converter material, or microbeads of transparent neutron-specific scintillator such as Li-glass or borosilicate glass scintillator, all embedded in a transparent hydrogenous matrix such as PMMA. Alternatively, the detectors 101-102 may include a thin semiconductor type detector coated with a neutron-capture nuclide such as boron or lithium, so that the ions emitted by the capture nuclide may pass into the semiconductor. As a further alternative, the detectors 101-102 may include gaseous ionization detectors such as proportional chambers or Geiger tubes filled with a gas such as $^3$He or $BF_3$, and/or coated on the interior surface with boron or lithium.

In some embodiments, the detectors 101-102 may include ionization-density-dependent material such as PSD scintillators, thereby providing separate information about gamma rays and neutrons according to the different pulse shapes that they generate in the ionization-density-dependent material. Alternatively, the detectors 101-102 may include boron or lithium coated gaseous detectors such as proportional detectors that enable neutron-gamma discrimination according to pulse height or other signal property. By separately analyzing the gamma and neutron interactions, some embodiments can detect a gamma ray source and a neutron source simultaneously, and may also localize one or both sources simultaneously. This may be a crucial advantage in a situation where both neutron and gamma emitters are present, such as a reactor accident or a clandestine weapon hidden by a benign gamma ray emitter for example.

In some embodiments, the middle detector 102 may be slab-shaped, and it may be oriented perpendicular to the aiming plane 120 as shown in the figure. In other embodiments, the middle detector 102 may have a square shape, or a rectangular cross-section with the longitudinal dimension larger than the lateral dimension, or other suitable shapes. In some embodiments, the position of the middle detector 102 relative to the side detectors 101 may affect the angular sensitivity of the middle detector 102, due to the partial blocking action by the side detectors 101 for particles 111 that arrive from high angles. In one embodiment, the middle detector 102 may be positioned flush with the front 106, such that the front surface of the middle detector 102 is substantially coplanar or coterminous with the front surfaces of the side detectors 101, wherein "substantially coplanar" means coplanar within a small distance such as within $\frac{1}{10}$ or $\frac{1}{4}$ or $\frac{1}{2}$ times the thickness of the middle detector 102. In another embodiment, the middle detector 102 may be recessed from the front 106, such that the front surface of the middle detector 102 is placed rearward relative to the front surfaces of the side detectors 101 by a "recess distance." In some embodiments, the recess distance may be 0.1 or 0.5 or 1.0 or 2.0 times the separation distance between the side detectors 101. In some embodiments, the middle detector 102 may protrude frontwardly beyond the front surfaces of the side detectors 101 by a protrusion distance, such as 0.1 or 0.5 or 0.9 times the thickness of the middle detector 102. In some embodiments, the angular sensitivity distribution of the middle detector 102, as modified by the side detectors 101, may result in an angular correlation function that provides an approximately linear relationship that determines source angles 112 ranging from zero to ±90 degrees, thereby enabling localization of the source 110 throughout the front half-space. Positive source angles represent sources on one side of the aiming plane 120 and negative source angles represent sources on the other (opposite) side of the aiming plane 120, and a source angle of substantially zero represents a source substantially aligned with the aiming plane 120. "Substantially zero degrees" means zero degrees within 1 or 2 times the angular resolution of the system. A source is "substantially aligned" with the aiming plane 120 if the source position is in the aiming plane 120 within 1 or 2 times the angular resolution of the system.

The middle detector 102 may have a slab shape with a width greater than its thickness, such as 4 or 10 times or more times its thickness, configured for example to tailor the angularسensitivity. Alternatively, or in addition, the width of the middle detector 102 may be greater than the average interaction distance of the particles therein, such as 2 or 10 or more times the average interaction distance, and the thickness of the middle detector 102 may be less than the average interaction distance, such as 0.5 or 0.1 or less times the average interaction distance of the particles therein. The "average interaction distance" is the average projected distance that the particles travel in the material of the middle detector 102 before detectably interacting, such as the scattering mean free path of a high-energy neutron, the projected capture distance of a thermalized neutron, or the inverse mass attenuation factor of a gamma ray.

Conventional detectors typically have a longitudinal ambiguity, in which they cannot determine whether the source 110 is in front or behind, due to symmetry. Embodiments of the presently disclosed system have no such defect. For example, the embodiment of FIG. 1 breaks the longitudinal ambiguity since the middle detector 102 is closer to the front 106 than the back 107, and therefore has a higher counting rate when the source 110 is in front of the system, and a lower counting rate when the source 110 is behind the system. The processor 105 may be configured to determine whether the source 110 is in front or behind the system by calculating the sum of the two side detector 101 rates, dividing the middle detector 102 rate by that sum, and then comparing that result (or its inverse) to an expected range of values for a source 110 being in front or behind the system.

The processor 105 may include a digital calculating device such as a microcontroller or CPU or GPU or logic array or the like, configured to process the detector output signals 113 and determine the location of the source 110. The processor 105 may be embedded in the system, or it may be mounted externally, or there may be multiple separate processors such as an embedded microcontroller internal to the system communicating with a facility computer elsewhere. In some embodiments, the processor 105 may be programmed to perform one or more of the angular analysis methods detailed herein, and further configured to indicate the calculated source angle 112 using a human-readable display or indicator, and may store the results in a non-transitory computer-readable record and/or transmit the results to an external computer.

To consider a specific example adapted to detect 0.5 MeV gamma rays, the side detectors 101 may be PVT plastic scintillator with a thickness of 35 mm and a width (in the back-to-front direction as depicted) of 75 mm. The length (going into the page as depicted) of the side detectors 101 may be 150 mm for a portable unit. For a large installation such as a cargo scanner, the length of the side detectors 101 may be much larger, up to four meters (assuming the signal is collected efficiently). Such a tall detector may be able to scan an entire vehicle or inspection zone at once.

The middle detector 102 may be, for example, a LYSO scintillator with dimensions 5 mm thick by 30 mm wide, and a length equal to that of the side detectors 101. The middle detector 102 may be oriented perpendicular to the side detectors 101, and parallel to the front surface 106 of the system. In the depicted embodiment, the front surface of the middle detector 102 is flush or coplanar with the front surfaces of the side detectors 101.

As a second exemplary embodiment, the particle 111 may be a neutron such as a low-energy (thermal or epithermal, E<1 eV) neutron. The side detectors 101 may be gaseous ionization tubes such as proportional chambers containing a neutron-capture gas such as $^3$He or $BF_3$ or other arrangement of neutron-capture nuclei. The side detectors 101 may include one or multiple wire grids at a positive high voltage, proximate to cathode electrodes coated with boron or lithium for example. The side detectors 101 may be large enough to have a high probability (such as greater than 30% or 50% or 80%) of scattering or absorbing the neutrons. Alternatively, the side detectors 101 may include multiple such anode grids and cathode electrodes in sequence, which may provide high detection efficiency as well as improved contrast by preventing neutrons from passing through and being detected in the opposite side detector 101. The middle detector 102 may be an ion-implanted or surface-barrier type semiconductor detector and may include capture nuclei such as LiF or $B_4C$, which may be arranged internally in the chamber or as a thin layer, to promote neutron capture reactions that generate energetic ions.

As a third exemplary embodiment, the particle 111 may be a 1 MeV neutron, the side detectors 101 may be HDPE containing ZnS-coated optical fibers to detect recoil protons, or PMMA containing microbeads of a transparent scintillator for the same purpose.

The processor 105 may be configured to calculate the source angle 112 from the various detector rates. For example, the processor may first accumulate detection data such as counting rates from the detectors 101-102 for a period of time, and may calculate a "differential" equal to the detection rate of one of the side detectors 101 minus the detection rate of the other side detector 101. The processor 105 may divide the differential by the detection rate of the middle detector 102, thereby obtaining a ratio. The processor 105 may use a predetermined angular correlation function that takes the ratio value as input and estimates the source angle 112 as output. In this way, the processor 105 may determine the source angle 112 from a single set of detection data, without iterations or rotations, according to some embodiments.

Cosmic rays are energetic particles, mostly muons at sea level, traveling generally vertically through the atmosphere, resulting in a background counting rate in each detector. In the usual orientation of the system, for measuring the horizontal angle of the source 110, the side and middle detectors 101-102 are vertical, and therefore are hit by fewer cosmic ray particles than if they were horizontal. In addition, each cosmic ray particle is likely to pass through an extended region of the detector 101 or 102, and therefore to deposit a lot of energy, resulting in large pulses 113 that can be rejected on the basis of pulse height alone. For example, a scintillator may have a vertical dimension of between 5 and 15 cm which would be typical for a small device, and with a thickness of typically 1-3 cm. Depending on the cosmic ray angle, the path of the cosmic ray through the scintillator is tangentially more than the thickness, such as at least 4 cm typically. Most cosmic rays drop energy at a rate of about 2 MeV per gram/cm$^2$ of material traversed, or at least 8 MeV in 4 cm of travel through a plastic scintillator which has a density of about 1 gram/cm$^3$. Most of the gammas from nuclear reactor materials, weapon materials, industrial and medical isotopes, and the like are much lower in energy, typically 1-2 MeV. Therefore, even with the relatively poor energy resolution of plastic scintillators, most of the cosmic rays can be rejected by a threshold cut at 3-5 MeV.

As a further background reduction, any events that trigger more than one detector 101-102 may be vetoed or rejected. Cosmic rays usually travel all the way through the system and thus are likely to hit more than one detector 101-102. Such a coincidence veto can eliminate many cosmic rays. As an additional advantage, the coincidence veto can also eliminate events in which a neutron or gamma ray scatters in one side detector 101, and then scatters in the other side detector 101.

Figure 2:
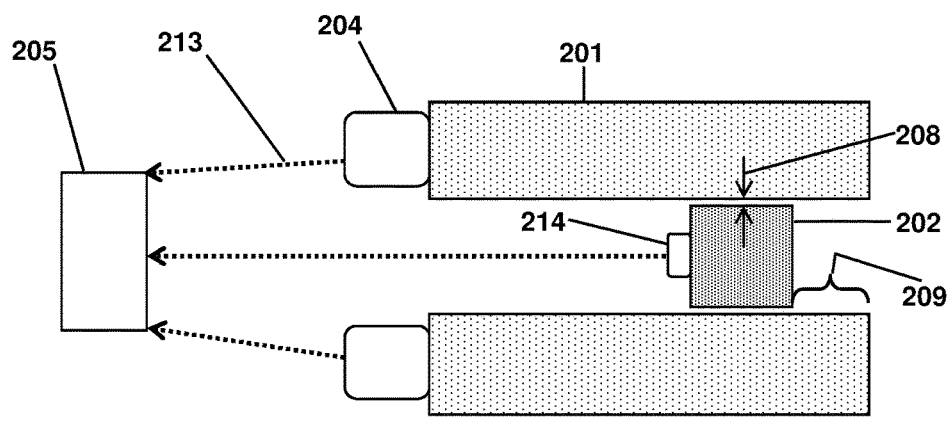
FIG. 2 is a cross-section sketch of an exemplary system with a recessed middle detector and with light sensors conveying data to a processor according to some embodiments.

FIG. 2 shows a cross-section view of an exemplary embodiment of the present system with improvements. Two side detectors 201 are shown surrounding the middle detector 202. The side detectors 201 and the middle detector 202 are scintillators in this example. Light sensors 204 such as phototubes can view the side detectors 201, and a photodiode light sensor 214 can view the middle detector 202. The light sensors 204 and 214 may be mounted on the rear surface of each detector 201-202, thereby avoiding the placement of material in the way of incident particles from the front half-space. Signals depicted as dotted arrows 213 are passed from the light sensors 204 and 214 to a processor 205 for analysis. In the embodiment depicted, the middle detector 202 is shown separated from the side detector 101 by a small separation distance 208 such as 0.5 mm, and recessed from the front of the side detectors 201 by a recess distance 209, which in this example is 15 mm. In some embodiments, the angular correlation function may depend on the separation distance 208, and on the shape of the middle detector 202, and on the recess distance 209. The middle detector 202 in the depicted example has a square cross-section.

The processor 205 may include analog signal processing electronics such as amplifiers, electronic filters, pulse-height discriminators, pulse-shape analyzers and the like, as well as digital computing electronics capable of performing calculations according to a method such as the various analysis methods detailed herein. In some embodiments, the method may include counting the pulses from each detector 201-202 for a particular time interval, performing arithmetic operations to derive the source angle from the data, and indicating or transmitting or otherwise reporting the results. Microcontrollers of many different types, CPUs and GPUs, gate arrays and ASICs of many types may be used for this purpose according to various embodiments.

Figure 3:
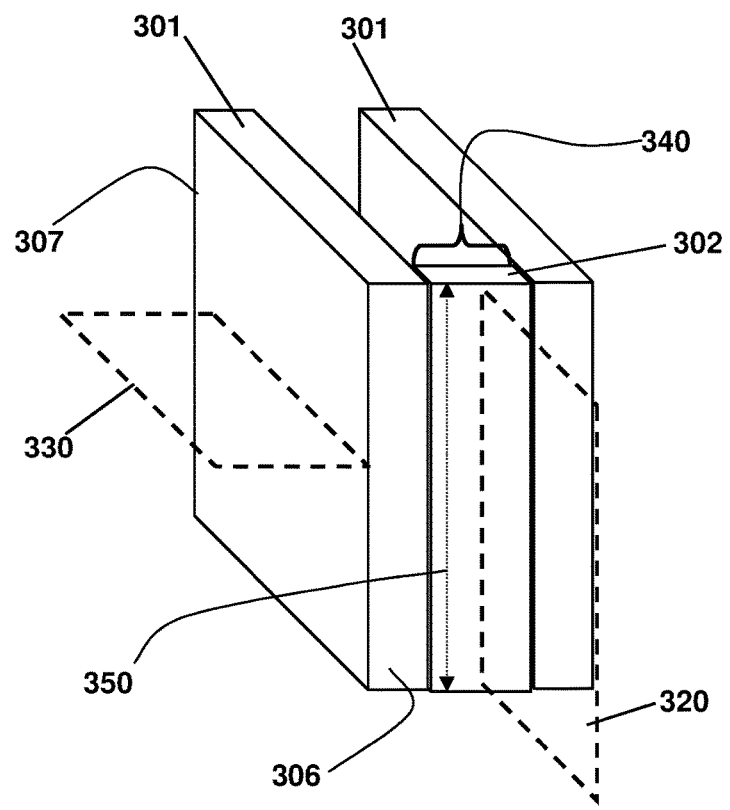
FIG. 3 is a sketch in perspective of an exemplary system facing out of the page according to some embodiments.

FIG. 3 is a perspective sketch of the embodiment of FIG. 2 but with the middle detector 302 now slab-shaped and flush with the front 306 of the side detectors 301. The system is pointing out of the page, generally toward the viewer's right side. The aiming plane 320, shown in dash, is a centrally positioned plane of symmetry parallel to the side detectors 301. The midplane 330 is a plane passing centrally through the system, perpendicular to the aiming plane 320 and perpendicular to the front 306 of the system. The back of the system is indicated as 307. The width of the middle detector 302 is indicated by a curly brace 340, and the height or length of the middle detector 302 is indicated by an arrow 350.

The middle detector 302 may have a symmetrical angular sensitivity distribution, which is maximal for sources in the forward direction (that is, aligned with the aiming plane 320). In contrast, the side detectors 301 can have antisymmetric angular sensitivities relative to the aiming plane 320. As a result of this difference in angular sensitivities, there may exist an angular correlation function that quantifies the correlation between the source angle and the detection rates.

Figure 4:
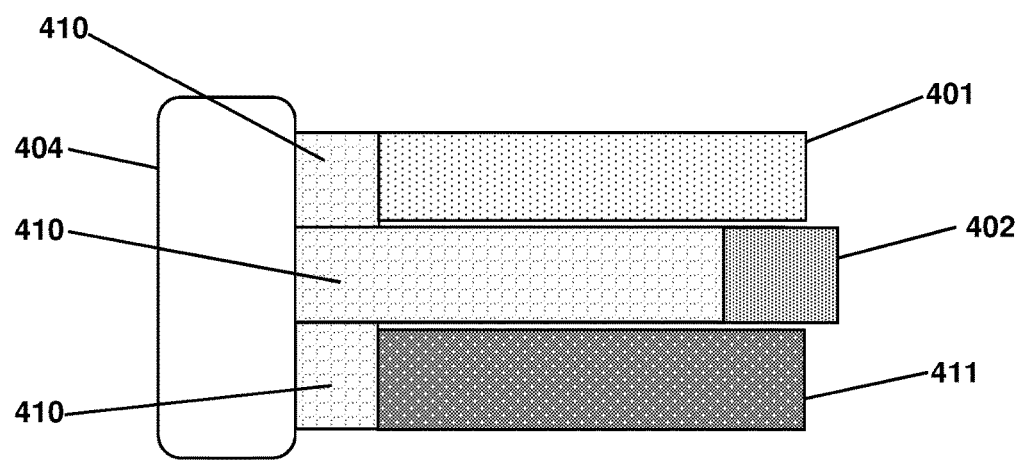
FIG. 4 is a cross-section sketch of an exemplary system with detectors comprising three scintillators of different types and a shared light sensor according to some embodiments.

FIG. 4 is a cross-section sketch of an exemplary embodiment of the system in which the two side detectors 401 and 411 are made from two different scintillator materials that produce different pulse shapes. For example, the first side detector 401 (light stipple) may be PVT and the other side detector 411 (dark stipple) may be BGO, which have pulse decay times of 5 ns and 300 ns respectively. Likewise, the middle detector 402 may be made from yet a third scintillator material with a distinct pulse shape, such as $CdWO_4$ with a pulse decay time of 1 to 14 microseconds. A single light sensor 404, such as a large-diameter phototube, may view both side detectors 401 and 411, and also the middle detector 402, through light guides 410 (light grid hatch). The signals from the various detectors are distinct in that they can be separated according to pulse shape, thereby indicating which detector detected each particle. In addition, a precalibrated detection efficiency and/or a predetermined background rate may be applied as corrections for each detector. The configuration may be economical since only a single light sensor 404 is needed.

The middle detector 402 is shown rectangular in shape and protruding beyond the side detectors 401. With such a protruding position, the middle detector 402 may have a higher detection efficiency for particles arriving at various angles, but with a smaller difference between the zero-degree and 90-degree angular response. Designers can choose the detector shape and the amount of detector protrusion according to the relative importance of wide-angle efficiency versus narrow-angle resolution.

Figure 5:
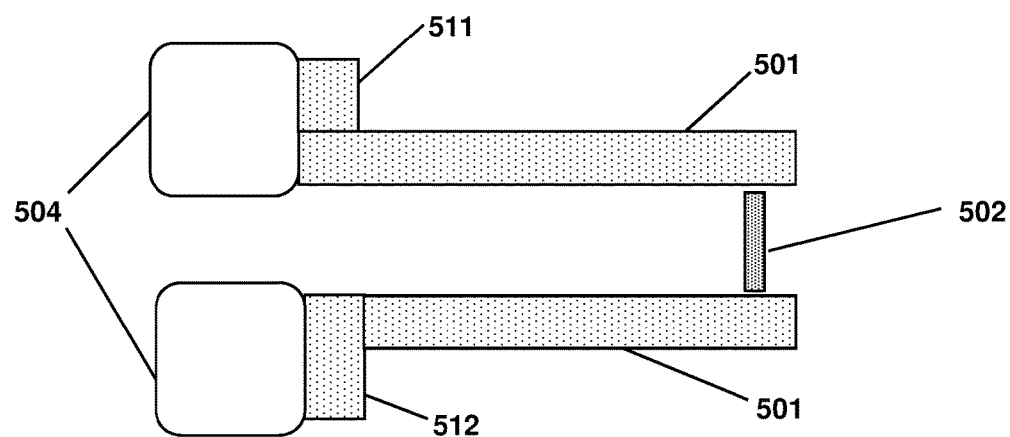
FIG. 5 is a sketch in cross-section of an exemplary system with the addition of detector back-flanges according to some embodiments.

FIG. 5 shows an exemplary embodiment of the system including detector back-flanges 511 and 512 and a middle detector 502. Here the side detectors 501 are rather thin, comprising a high-density scintillator material such as LYSO for example. LYSO has a high detection efficiency for gamma rays and a correspondingly high blocking fraction to prevent gamma rays from passing through to the other side detector 501. Due to the high density, a relatively thin layer may be sufficient to detect incoming gamma rays from most angles. However, when the system is brought into alignment with a gamma ray source, very few gammas are observed in the thin side detectors 501 due to the small area presented edge-wise to the gamma ray source. That could make it difficult for the processor to determine when the system becomes aligned with the source, due to the reduced counting rates in the two side detectors 501. To provide additional detection area when the system is aimed at the source, the back-flanges 511 and 512 can be mounted on the rear portions of the two side detectors 501. The back-flanges 511 and 512 may extend laterally beyond the adjacent side detectors 501 by a distance, which is preferably at least equal to the thickness of the adjacent side detectors 501, and may be larger. Thus, the back-flanges 511 and 512 may provide extra detection area when the system is aligned with the source.

The figure shows one back-flange 511 comprising a segment mounted onto the exterior surface of a side detector 501, and a second back-flange 512 comprising a larger segment mounted behind the adjacent side detector 501 according to some embodiments. As another option, the side detector 501 and its back-flange 511 or 512 may be made as a single L-shaped part. All of these options perform similarly. Each light sensor 504 can view one side detector 501 and its back-flange 511 or 512 together.

While the detector materials listed in this example are mainly scintillators applicable to gamma rays, the same principles may be used for improving the low-angle detection efficiency of high-energy or low-energy neutrons using suitable neutron-sensitive detector materials and/or other detector types. For example, a low-energy neutron detector based on neutron capture in a thin layer of B or Li, which is proximate to an ionization chamber or thin scintillator, may have even thinner dimensions than indicated in the figure, and thus would benefit from back-flanges to detect low-energy neutrons from sources near zero degrees.

Figure 6:
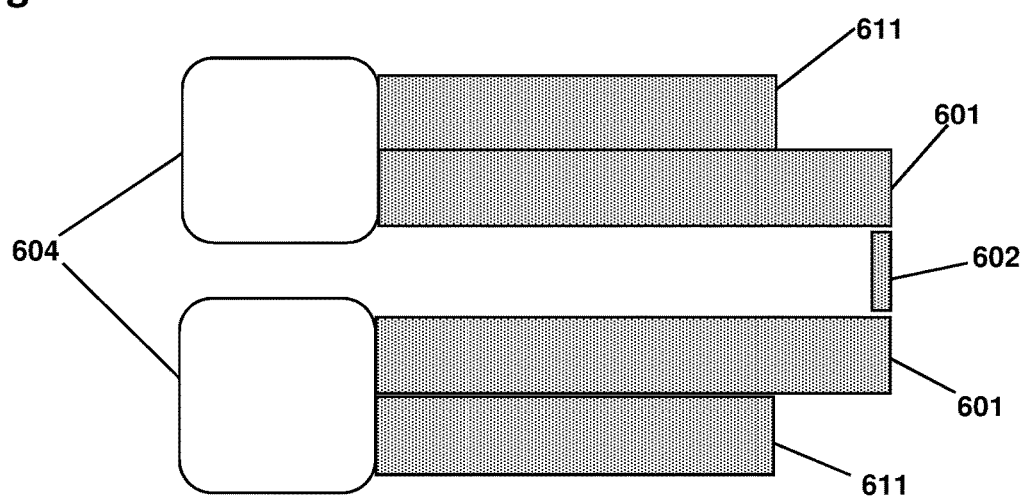
FIG. 6 is a sketch in cross-section of an exemplary system with outriggers to augment the detection efficiency according to some embodiments.

FIG. 6 shows an exemplary embodiment of the system, now with outriggers 611 comprising detector panels mounted adjacent to the exterior surfaces of the side detectors 601. The outriggers 611 may be planar slabs of detector material, which may be the same material as the side detectors 601 or a different detector material, depending on the application. A purpose of the outriggers 611 may be to increase the detection efficiency by providing more detection volume. A second purpose may be to decrease the fraction of incident particles that pass through into the opposite side detector. In a preferred embodiment, each outrigger 611 may be cut shorter than the adjacent side detector 601, to avoid detecting obliquely-arriving particles that pass in front of the side detectors 601. Thus, the front end of the outrigger 611 may be substantially shortened relative to the front end of the adjacent side detector 601. The outrigger shortening distance may be related to the thickness of the outrigger 611, for example being equal to the thickness of the outrigger 611. When so configured, the outriggers 611 may provide enhanced detection efficiency due to the larger detection volume, while causing little or no loss in angular resolution due to being cut away at the front end. The side detectors 601, middle detector 602, and the outriggers 611, may be made from scintillators that detect gamma rays or neutrons or both. Each side detector 601 and its adjacent outrigger 611 may be viewed together by a single light sensor 604 as shown. The outriggers 611 can nearly double the detection volume and thereby reduce the fraction of particles that trigger both side detectors 601.

Figure 7:
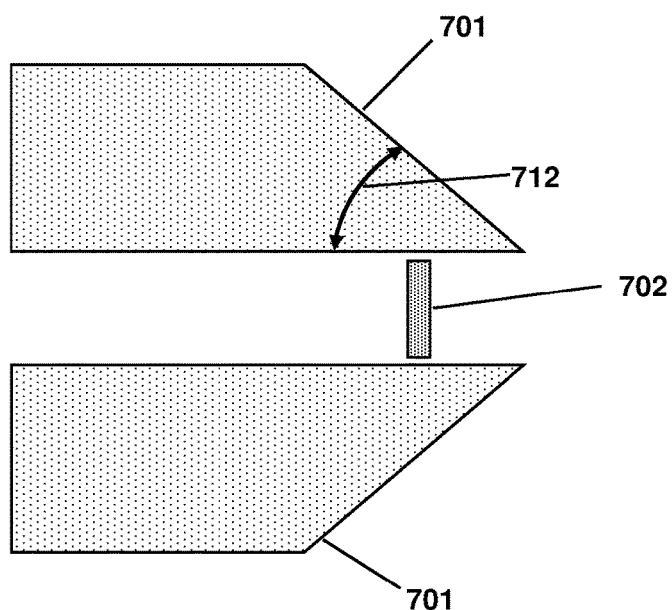
FIG. 7 is a sketch in cross-section of an exemplary system with trapezoidal side detectors according to some embodiments.

FIG. 7 shows an exemplary embodiment in which the side detectors 701 are gaseous ionization chambers configured for neutron detection. Each side detector 701 is shaped as a trapezoid in this top-view cross-section, with a front surface beveled at a bevel angle 712 relative to the aiming plane, which is typically 30 to 60 degrees. The trapezoidal shape can maximize the detection volume and accommodate multiple layers of wire grids and coated cathode electrodes, thereby enhancing detection efficiency while maintaining directional angular sensitivity. The middle detector 702 may be a lithium-coated semiconductor detector in this example, mounted between the side detectors 701. With such shaping, the trapezoidal side detectors 701 can be made much thicker, and thereby achieve greater detection efficiency, without sacrificing contrast between the two side detectors 701.

Figure 8:
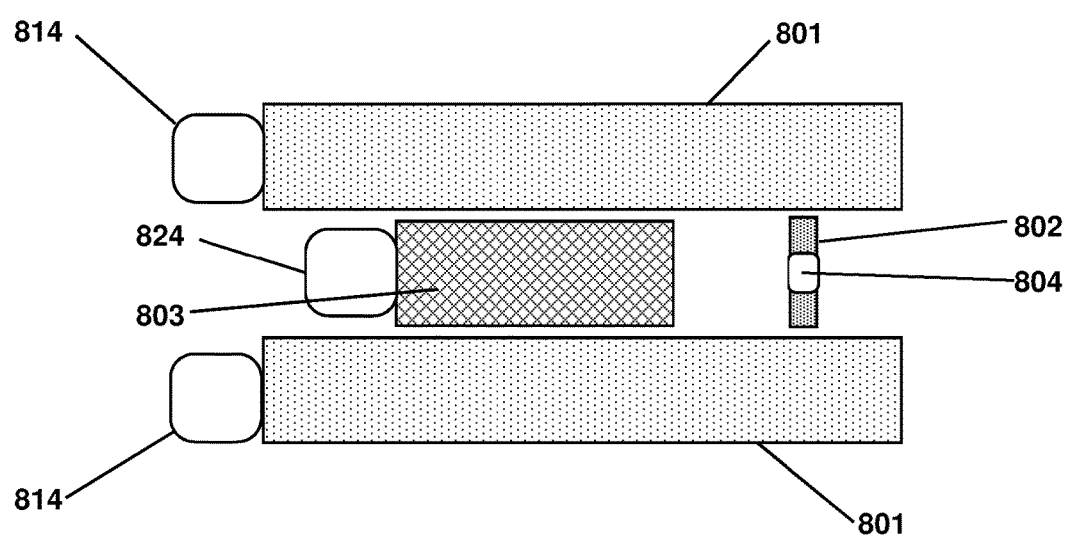
FIG. 8 is a sketch in cross-section of an exemplary system with an additional detector behind the middle detector according to some embodiments.

FIG. 8 is a cross-section sketch of an exemplary embodiment of the system including a fourth detector 803 positioned between the side detectors 801, behind the middle detector 802. Also shown are a photodiode light sensor 804 viewing the middle detector 802 from the top (that is, out of the page in this cross-section top view), and phototubes 814 viewing each of the side detectors 801. The phototubes 814 are shown mounted toward the back of the system, while the photodiode 804 views the middle detector 802 from the top surface. The fourth detector 803 is read out by an appropriate sensor 824. If the fourth detector 803 is a scintillator, the sensor 824 may be a light sensor; and if the fourth detector 803 is a semiconductor or gaseous ionization detector, the sensor 824 may be an amplifier circuit.

In some embodiments, the fourth detector 803 may be a spectroscopic or energy-resolving detector configured to measure the energy of incoming particles that pass through the thin middle detector 802. The energy-resolving fourth detector 803 may detect source particles primarily when the system is aimed at the source. The energy spectrum measured by the energy-resolving fourth detector 803 may thereby identify the source isotope, based on the energies observed. According to some embodiments, the energy-resolving fourth detector 803 may be, for example, a slab of NaI or other scintillator, or an HPGe or GeLi semiconductor detector, or a gaseous ionization chamber with linear charge collection. Preferably the energy-resolving fourth detector 803 has an energy uncertainty of 10% or less, wherein the energy uncertainty may be, for example, the full-width-at-half-maximum of a full-energy peak in the energy spectrum.

In other embodiments, the fourth detector 803 may be configured to detect the same type of particle as the middle detector 802, or a different particle type. For example, the side and middle detectors 801-802 may be configured to detect neutrons, and thereby to determine the location of a neutron source, while the fourth detector 803 may be configured to detect gamma rays and measure the energy spectrum of the gamma rays, thereby providing additional information about the source.

As a further option, in some embodiments, the side detectors 801 and/or the middle detector 802 and/or the fourth detector 803 may include a material that emits a first signal upon detecting a lightly-ionizing particle such as an energetic electron, and a second signal different from the first signal when detecting a heavily-ionizing particle such as an energetic ion. For example, the material of the side or middle or fourth detector 801-803 may include a scintillator such as a PSD scintillator, configured to produce a first light pulse upon detecting a Compton electron, and a second light pulse different from the first light pulse upon detecting a recoil proton or an alpha or triton from a neutron-capture event. Thus the initial particle may be identified as a neutron or a gamma ray according to the ionization density of tracks within the material. Exemplary PSD scintillators include CsI(Tl), certain elpasolites, and plastic scintillators with a special fluor, or alternatively ZnS which is mainly sensitive to energetic ions. Such a PSD scintillator can discriminate between gamma ray events and neutron events, since recoil protons and ions from neutron capture events have a high ionization density, whereas gamma-generated electrons have a low ionization density. The pulse properties of each event can indicate whether the event was due to a gamma ray or a neutron.

As a further option, in some embodiments, the fourth detector 803 may be configured to detect a first particle type and the side and/or middle detectors 801-802 may be configured to detect a second particle type different from the first particle type. For example, the fourth detector 803 may include a ZnS-based scintillator mingled with B or LiF that detects neutrons by capture and is nearly gamma-blind, while the side detectors 801 may be a hydrogen-free scintillator such as $CaF_2$ which has low neutron sensitivity. The fourth detector 803 can thus reveal a neutron source if present, while the other detectors can detect a gamma ray source and determine its location.

Figure 9:
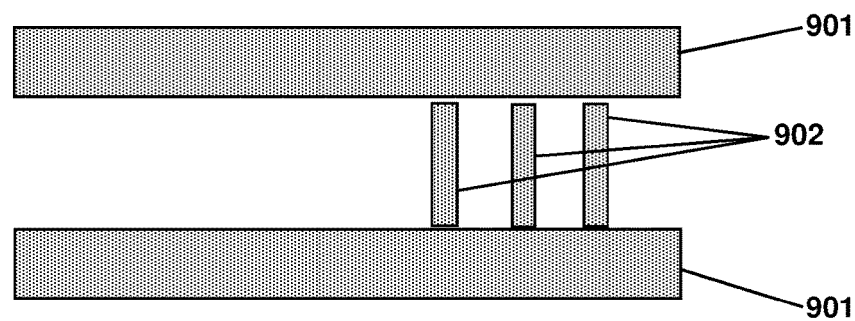
FIG. 9 is a sketch in cross-section of an exemplary system with three middle detectors according to some embodiments.

FIG. 9 is a cross-section sketch of an exemplary embodiment of the system wherein the middle detector is a member of a plurality of similar front-facing middle detectors 902, mounted sequentially between the side detectors 901 and closer to the front of the system than the back. Each of the plurality of middle detectors 902 is shown in this depiction as a slab-shaped form, perpendicular to the aiming plane and to the midplane, parallel to the front of the system, and configured to detect the particles and to produce a responsive signal. A purpose of using a plurality of middle detectors 902 may be to obtain higher detection efficiency. Each detector of the plurality of middle detectors 902 can contribute data for determining the source angle.

In other embodiments, the system may include a plurality of middle detectors positioned toward the front, and a plurality of rear-facing detectors positioned toward the back, and all oriented perpendicular to the aiming plane and perpendicular to the midplane. Such pluralities of middle detectors and rear-facing detectors may provide enhanced detection efficiency for particles arriving from the back as well as the front.

Figure 10:
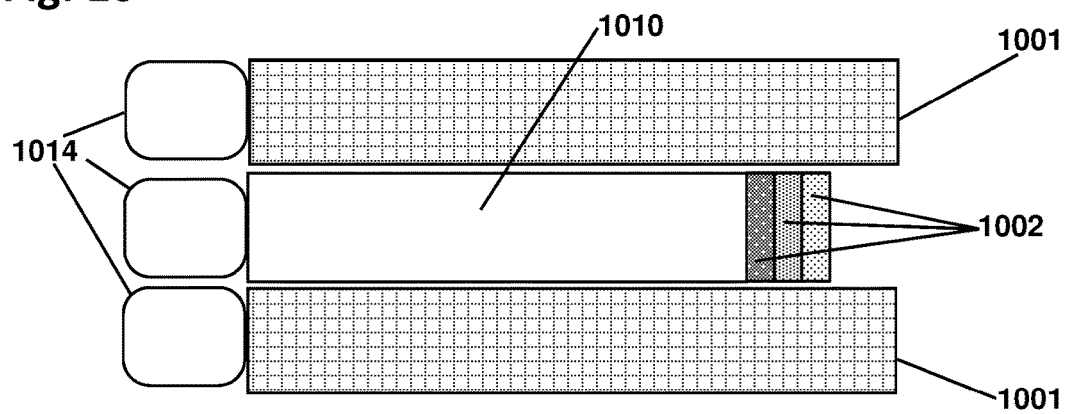
FIG. 10 is a sketch in cross-section of an exemplary system with three middle detectors comprising scintillators of different types, optically coupled together and viewed by a common light sensor according to some embodiments.

FIG. 10 shows an exemplary embodiment of the system in which the side detectors 1001 may be energy-resolving scintillators (light cross-hatch) and the middle detector may be a member of a plurality of similar front-facing middle detectors 1002, each configured to detect the particles and emit a signal. The plurality of middle detectors 1002, here including three middle detectors 1002, are mounted closer to the front of the system than the back, perpendicular to the aiming plane and to the midplane, parallel to the front of the system, and configured to detect the particles. As indicated by different stipple densities in the figure, each member of the plurality of middle detectors 1002 is a different scintillator material, each such material being configured to produce a different pulse shape; hence using pulse shape analysis, each detection event can be allocated to whichever of the plurality of middle detectors 1002 was active. As shown, the middle detectors 1002 are optically coupled to each other in a "phoswich" arrangement, which is optically coupled to a light guide 1010. Light sensors 1014 may be connected to the light guide 1010 and to each side detector 1001. Thus embodiments the system may determine the source angle by analyzing signals from each of the plurality of middle detectors 1002 separately.

The side detectors 1001 in the depicted example may be energy-resolving scintillators, as mentioned. Energy spectra from the side detectors 1001 may thus be used to identify the source isotope. As a further option, the light guide 1010 may be made of a transparent high-density material such as leaded glass, thereby providing additional isolation between the side detectors 1001.

Figure 11:
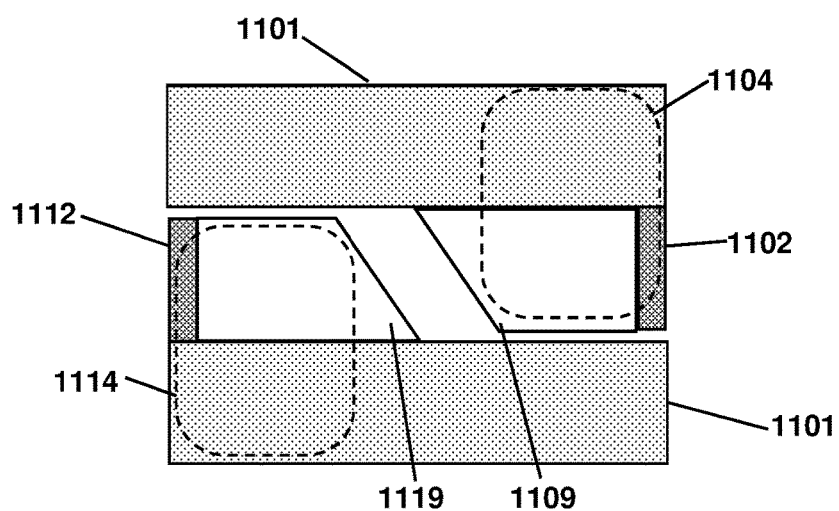
FIG. 11 is a cross-section sketch of an exemplary system including a rear-facing detector and light guides according to some embodiments.

FIG. 11 is a cross-section sketch of an exemplary embodiment of the system including two side detectors 1101, a middle detector 1102, a rear-facing detector 1112, two light guides 1109 and 1119, and two light sensors 1104 and 1114 (shown dashed). The light sensors 1102-1114 may be mounted on the top or on the bottom of the system (perpendicular to this cross-section view). The middle detector 1102 is shown at the front of the system and flush with the front surfaces of the side detectors 1102. The rear-facing detector 1112 is identical in form to the middle detector 1102, and is shown at the back of the system and flush with the back surfaces of the side detectors 1101. The middle detector 1102 and the rear-facing detector 1112 may be made of a first scintillator type as shown in dark stipple, while the side detectors 1101 may be made of a different scintillator (light stipple) which produces a different pulse shape. An advantage of the depicted embodiment may be that the system can detect and localize sources all around the system, both front and back, using signals from the middle detector 1102 or the rear-facing detector 1112 as appropriate. For example, if the detection rate in the middle detector 1102 is higher than in the rear-facing detector 1112, the source is likely in the front, and the source angle can be determined according to the detection rates of the side and middle detectors 1101-1102. If the detection rate in the rear-facing detector 1112 is higher than in the middle detector 1102, then the source angle can be determined according to the detection rates in the back and side detectors 1112-1101. In addition, when the source is exactly aligned with the aiming plane, both side detectors 1101 count at statistically the same rate. In that case the system can determine whether the source is in front or behind according to which of the middle 1102 and back 1112 detectors has the higher rate, without having to rotate the system or other artifice to discriminate front from back source locations.

The middle detector 1102 may be optically coupled to one of the side detectors 1101 and to a light guide 1109, which may be coupled to a light sensor 1104, which may be mounted on the top of the system. Also the rear-facing detector 1112 may be optically coupled to the other side detector 1101 and to the other light guide 1119, which may be coupled to the other light sensor 1114. An advantage of the depicted embodiment may be that only two light sensors 1104-1114 are needed, since they can monitor the activity in all four detectors 1101-1102-1112. The light guides 1109-1119 may help to collect light from the side detectors 1101 and either the middle 1102 or the rear-facing detector 1112 with improved uniformly. The light guides 1109-1119 may also partially block particles that pass through the middle detector 1102 and prevent them from reaching the rear-facing detector 1112, and vice-versa. The light guides 1109-1119 may also prevent particles from passing between the side detectors 1101, thereby reducing the number of rejected events.

Figure 12:
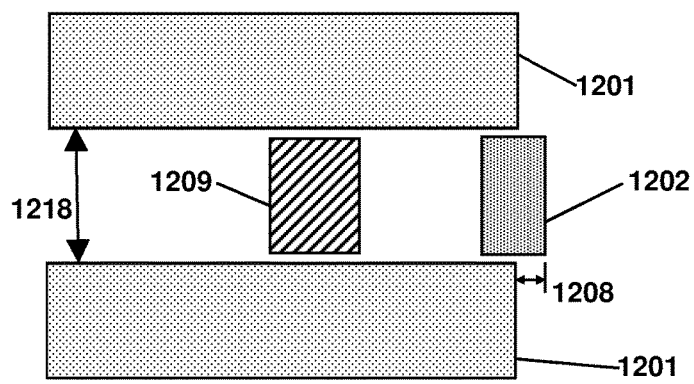
FIG. 12 is a sketch in cross-section of an exemplary system with a shield slug behind the middle detector according to some embodiments.

FIG. 12 is a cross-section sketch depicting an exemplary embodiment with two side detectors 1201, a middle detector 1202, and a shield slug 1209 positioned between the side detectors 1201 and behind the middle detector 1202. The middle detector 1202 is protruding frontward beyond the front surfaces of the side detectors 1201 by a distance 1208 which in this case is 0.2 times the separation distance 1218 between the side detectors 1201. The protrusion distance 1208 is also 0.5 times the thickness of the middle detector. The shield slug 1209 may prevent stray particles from reaching the middle detector 1202 from the back.

Figure 13:
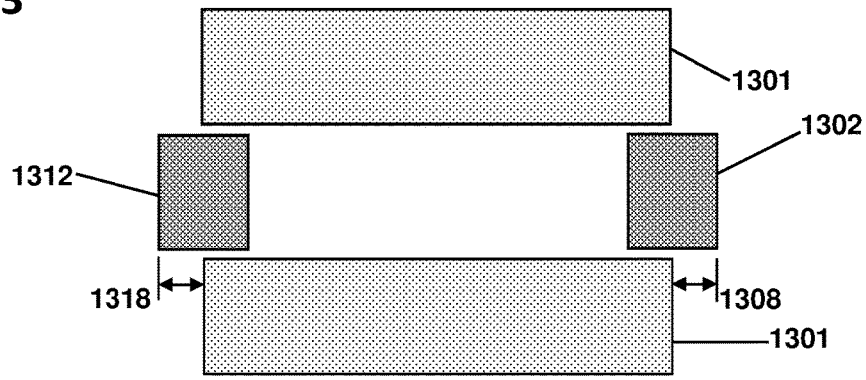
FIG. 13 is a sketch in cross-section of an exemplary system with a protruding rear-facing detector according to some embodiments.

FIG. 13 is a cross-section sketch depicting an exemplary embodiment including two side detectors 1301 and a middle detector 1302 and a rear-facing detector 1312. The middle detector 1302 is shown protruding frontwardly from the side detectors 1301 by a protrusion distance 1308, while the rear-facing detector 1312 is shown protruding rearwardly from the back surfaces of the side detectors 1301 by the same protrusion distance 1318. With the middle and rear-facing detectors 1302-1312 thus symmetrically positioned, the system can determine source locations front and back using the same predetermined angular correlation function.

Figure 14:
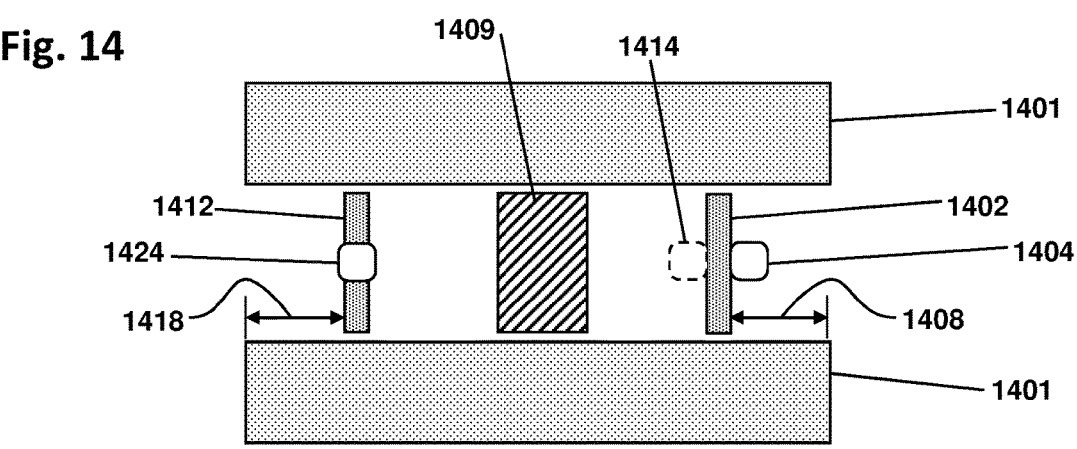
FIG. 14 is a sketch in cross-section of an exemplary system with a rear-facing detector and a central shield slug according to some embodiments.

FIG. 14 is a cross-section sketch depicting an exemplary embodiment of the system with two side detectors 1401, a middle detector 1402, a rear-facing detector 1412, and an optional shield slug 1409. The middle detector 1402 is shown recessed by a recess distance 1408 relative to the front surfaces of the side detectors 1401, while the rear-facing detector 1412 is shown recessed by a back recess distance 1418 relative to the back surfaces of the side detectors 1401. For symmetry, the two recess distances 1408 and 1418 may be made the same, and the shield slug 1409 may be positioned centrally to block particles from passing longitudinally through the system. With such symmetry, the system can detect and localize sources all around the system, according to some embodiments.

A small light sensor 1404 is shown coupled to the front surface of the middle detector 1402. If the light sensor 1404 is sufficiently small, it may block only an insignificant amount of incoming particles. Alternatively, as shown in dash, a light sensor 1414 may be mounted on the interior surface of the middle detector 1402, and likewise for the rear-facing detector 1412, thereby avoiding blocking any of the incoming particles. As a further option, a light sensor 1424 may be mounted on the top (or bottom or both) of the middle and rear-facing detectors 1402-1412, thereby avoiding blocking particles and providing easy access for maintenance, in some embodiments.

Figure 15:
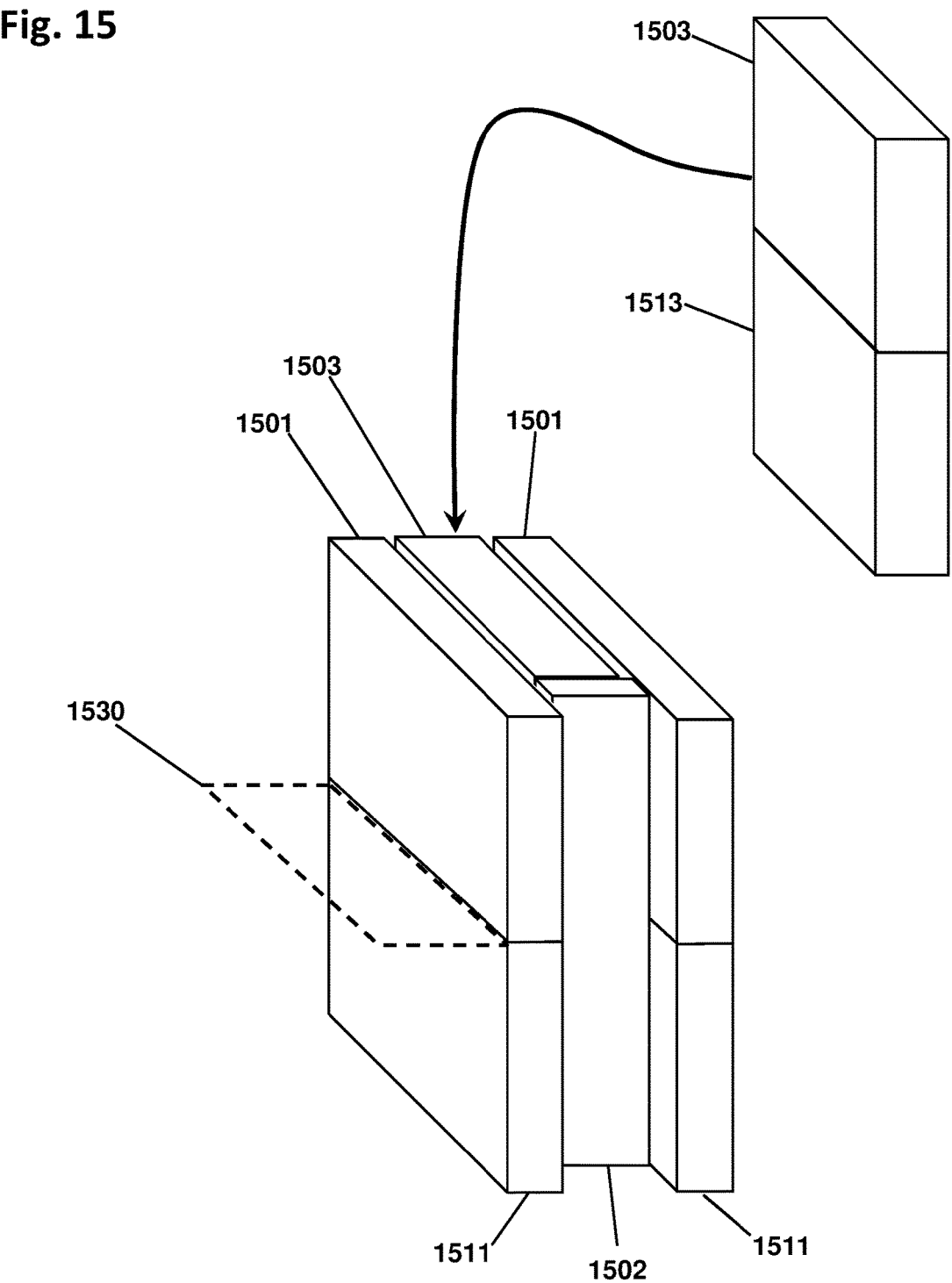
FIG. 15 is a sketch in perspective of an exemplary system with split detectors abutting at the midplane according to some embodiments.

FIG. 15 is a perspective sketch of an exemplary embodiment configured to determine whether the source is above or below or substantially on the midplane of the system, without having to turn the system on its side. In the sketch, the system is shown pointed toward the viewer's right side and out of the page. Each side detector may be split into two portions, an upper side portion 1501 and a lower side portion 1511, abutting edgewise at the midplane 1530 which is shown in dash. The upper and lower side portions 1501 and 1511 may be configured to emit signals upon detecting the particles from the source. According to some embodiments, if the source is above the midplane 1530, the upper side portions 1501 count higher than the lower side portions 1511, and vice-versa if the source is below the system. If the source is substantially on the midplane 1530, then the upper and lower side portions 1501 and 1511 may count at substantially the same rate. Thus, the system can compare signals from the upper and lower side portions 1501 and 1511 and thereby determine whether the source is above, below, or substantially on the midplane 1530, according to the ratio or difference of counts in the upper side portions 1501 versus the lower side portions 1511. As used herein, the source is substantially on a plane if the angle between the plane and the source is less than a predetermined small angle such as one degree or two degrees, or alternatively if the separation of the source from the plane is less than 1 or 2 times the resolution of the system. As used herein, the counting rates of two detectors are substantially the same if they differ by no more than an expected variation such as one or two times the statistical uncertainty.

Some embodiments can also determine the source angle by adding together the signals from the upper and lower side portions 1501 and 1511 on each side, thereby forming an effectively unsplit side detector for the purposes of analysis. The combined upper and lower side signals (or counting rates) thus effectively act as an unsplit left side detector and an unsplit right side detector, respectively. The left sum may be subtracted from the right sum, thereby obtaining a differential. The differential may be divided by the counting rate for the middle detector 1502, thereby obtaining a ratio. The ratio may be compared to the predetermined angular correlation function to determine the horizontal component of the source angle. In addition, the system may be configured to determine, when the counting rates in all four side detector portions 1501 and 1511 are substantially equal, that the system is aimed at the source both horizontally and vertically.

Alternatively, or in addition, the system may include a fourth detector, positioned behind the middle detector 1502. The fourth detector may be split into an upper detector 1503 and a lower detector 1513 abutting at the midplane 1530 in some embodiments. The upper and lower detectors 1503 and 1513 may be configured to detect the particles and responsively emit signals. (In the figure, the upper and lower detectors 1503 and 1513 are shown twice, once separated from the system by an arrow, and shown again positioned within the system, so as to show construction details.) The system may be configured to compare or subtract detection data from the upper and lower detectors 1503 and 1513, thereby determining whether the source is above, or below, or substantially on the midplane 1530.

As a further alternative, the fourth detector upper and lower portions 1503-1513 may be configured to detect a first particle type, while the side and front detectors 1501-1511-1502 may be configured to detect a different second particle type. The system may thereby indicate the presence of one particle type in the upper and lower detectors 1503-1513 while simultaneously detecting and measuring the source angle of the same source (or a different source) according to the detection rates in the upper and lower side portions 1501-1511. The depicted system may thereby reveal a complex distribution of sources. Moreover, the ratio of detections in the fourth detector upper and lower portions 1503-1513 may indicate whether a first source is above or below the midplane 1530, and simultaneously the upper and lower side detectors 1501-1511 can indicate whether the other source is above or below the midplane 1530. For example, with suitable choice of scintillators or other detector materials, the depicted system may detect a gamma ray source such as a benign $^{40}$K source, and determine its source angle, while at the same time detecting a separate neutron source such as a plutonium source, and determining that the neutron source is above or below the midplane, according to some embodiments. Such detailed particle-specific angular information about the radiation field may make it difficult for an adversary to conceal the presence of clandestine nuclear material.

Examples are presented next of several applications that may be greatly improved with the presently disclosed systems. In some embodiments, the system may be incorporated into a cargo inspection station of the type used for scanning trucks and maritime shipping containers to detect radiation sources. By indicating the longitudinal position of any sources detected, the system can greatly accelerate the inspection process. Embodiments of the system may enable an advanced hand-held radiation "survey" meter that indicates the direction of the source. In another embodiment, the system may be configured to detect radioactive contamination on personnel in a walk-through portal or a directional room/passageway monitor. In a further embodiment, the system may be incorporated in a mobile threat scanner of the type that measures radiation and detects threat materials while being driven through a region such as city streets.

Figure 16:
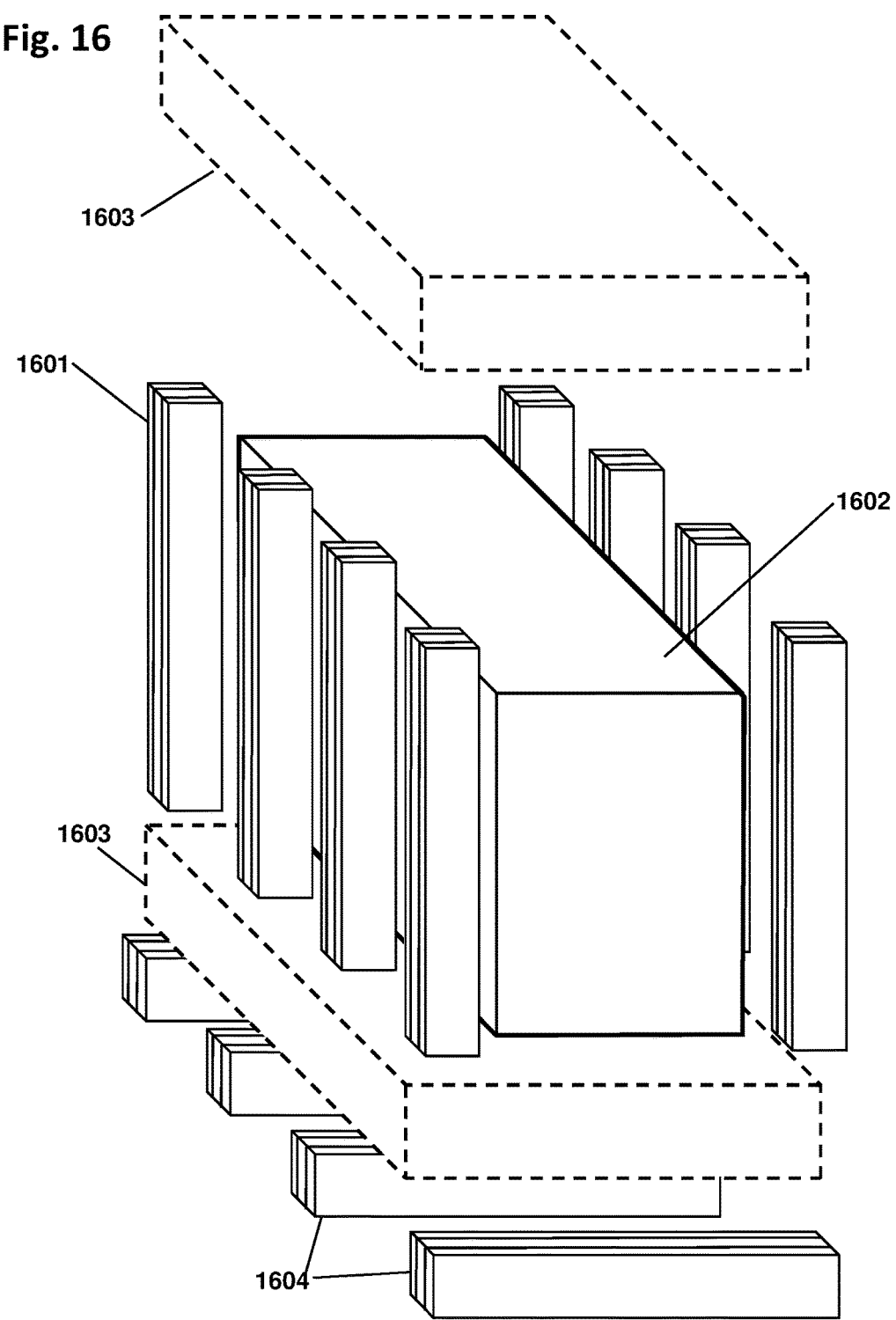
FIG. 16 is a perspective sketch of an exemplary vehicle inspection station incorporating multiple copies of the present system arrayed around an inspection zone according to some embodiments.

FIG. 16 is a perspective sketch of an exemplary vehicle and cargo scanner array comprising a large number of the present systems 1601 arrayed around an inspection object such as a shipping container 1602. The systems 1601 may be arranged on one side of the inspection zone, or both sides as shown, or above, or below 1604, or all around the inspection zone for maximum sensitivity. Each of the systems 1601 may be configured to detect gamma rays or neutrons from the container 1602 individually and to determine the horizontal angle of the source relative to each of the systems 1601, according to some embodiments. Alternatively, the detection data from all the systems 1601 may be analyzed together, for example as a global fit to the data using a source distribution model or other volumetric model. Such a global analysis is typically more sensitive and more accurate than simply analyzing the source angle determined by each system 1601 separately. Such a global analysis may be particularly advantageous when the source is shielded.

In a further embodiment, the array may include some systems 1601 mounted vertically, as depicted, to determine the horizontal position of the source, and others oriented horizontally to measure the elevation angle of the source. Then the data from all the detectors in the array may be input to a source model or other fitting routine which can determine the most likely location of the source or sources in three dimensions.

In a further embodiment, some of the systems 1601 may be configured to detect gamma rays, while others may be configured to detect neutrons. Alternatively, each of the systems 1601 may include ionization-density-dependent scintillators that discriminate between neutron and gamma events. In either case, the array can thereby determine (a) whether a gamma ray source is present in the cargo, (b) if so, where the gamma source is, (c) whether a neutron source is present in the cargo, and (d) if so, where the neutron source is. This information can enable much faster scanning and a much more reliable threat localization than non-directional detectors.

In a further embodiment, vehicles being inspected may pass through the inspection zone without stopping, although preferably at a low speed. The position of the vehicles may be measured continuously using a position sensing device such as an optical, RF, magnetic or another type of position sensor. The detector data can then be fit to a moving-source model.

In a further embodiment, a cosmic ray scattering-type vehicle inspection system may be provided, in which two cosmic ray tracking chambers 1603 (shown in dash) are positioned above and below the shipping container 1602. The cosmic ray tracking chambers 1603 may be configured to measure the amount of scattering of cosmic ray particles that pass through the shipping container 1602, and thereby reveal nuclear materials or shielding materials that produce anomalously high amounts of scattering. In one embodiment, any cosmic rays that pass through the systems 1601 may be flagged, so that the track can be corrected for extra scattering that may occur in passing through the systems 1601. Alternatively, the track analysis may select only those cosmic rays that do not pass through any of the systems 1601. As a further option, any events may be rejected if any of the systems 1601 is active at the same time as the tracking chambers 1603 detect a cosmic ray. As an even simpler alternative, the systems 1601 may be positioned laterally outside the field of view of the tracking chambers 1603, or below 1604 the tracking chambers 1603, thereby eliminating any interference.

The combination of a cosmic ray scattering inspection with a directional radiation detection array can provide many advantages. An adversary wishing to reduce the radiation signal may add more shielding around a weapon, but this would increase the amount of cosmic ray scattering and would thereby reveal the threat. Likewise the adversary could reduce the shielding to reduce the scattering signature, but this would greatly increase the amount of radiation detected. Thus the two types of inspections, working in cooperation, leave an adversary no design space for concealing the threat.

Figure 17A:
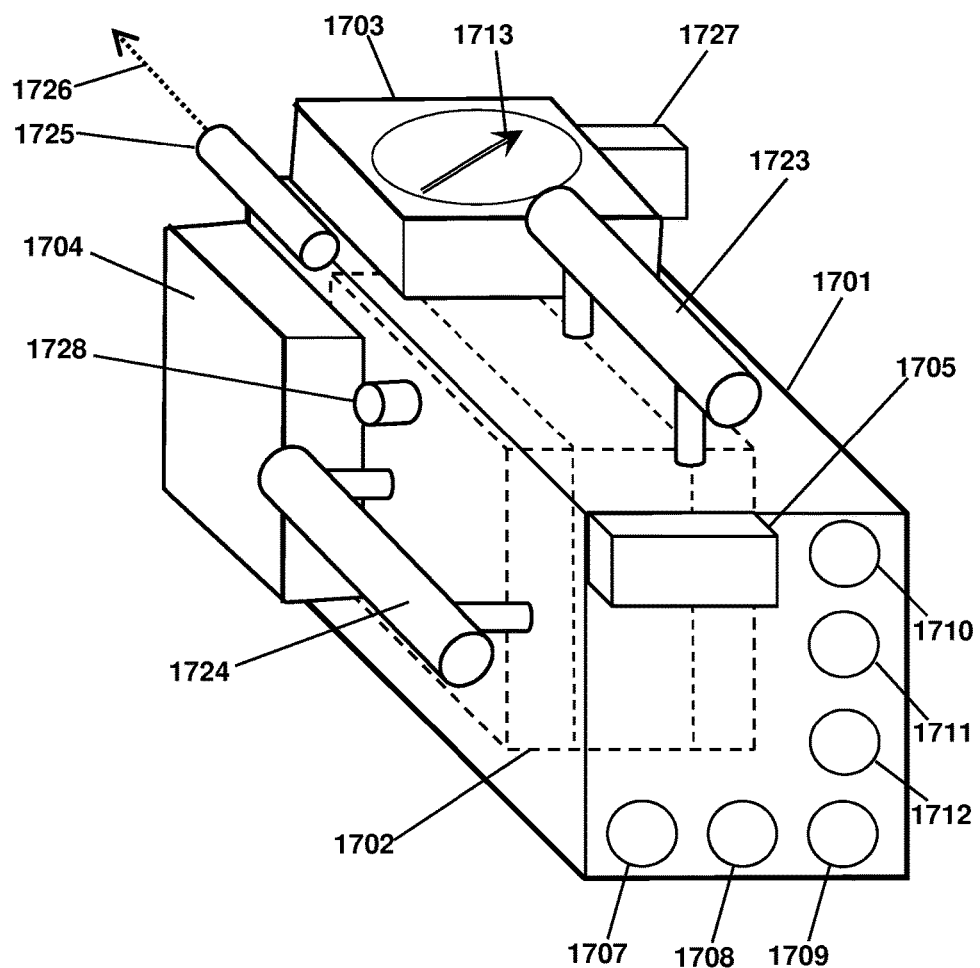
FIG. 17A is a perspective sketch of an exemplary portable directional survey meter according to some embodiments.

FIG. 17A is a perspective sketch of an embodiment of a portable radiation survey meter 1701 that can detect a radioactive source and also can indicate the direction of the source. The meter 1701 may include a system 1702 (hidden, shown in dash) with a processor 1705. In some embodiments, the meter 1701 may also include a first display 1703 and a first handle 1723 mounted on a first surface of the meter 1701, and a second display 1704 and a second handle 1724 mounted on a second surface of the meter 1701 which is orthogonal to the first surface. Thus the second handle 1724 and the second display 1704 are orthogonal to the first display and first handle 1703 and 1723. The orthogonal handles 1723 and 1724 thereby allow an operator to conveniently turn the meter 1701 on its side, and the orthogonal displays 1703 and 1704 allow the operator to observe the detection results during a horizontal angle scan or a vertical angle scan.

In some embodiments, the meter 1701 may be configured to display a rotatable icon 1713 pointing toward the calculated source location, which may be presented on whichever display 1703 or 1704 is currently on the uppermost surface of the meter 1701, or alternatively on both displays 1703-1704 simultaneously. The depicted meter 1701 may be useful for measuring the horizontal angle of a source and indicating its horizontal location to the operator using the first display 1703. When rotated 90 degrees on its side, the depicted meter 1701 may also measure the vertical angle of a source and indicate its vertical location to the operator using the second display 1704.

In some embodiments, the meter 1701 may include an electronic compass 1707, and/or a GPS receiver 1708, and/or a multi-axis accelerometer 1709. The compass 1707 may be configured to measure the geographical bearing of the meter 1701 which may enable the processor 1705 to determine when the meter 1701 is rotated horizontally. The processor 1705 may thereby relate the source angle to real-world coordinates of the detected source. The GPS receiver 1708 may be configured to determine the spatial position of the meter 1701, which the processor 1705 may record internally or transmit to an external receiver. Using the GPS data, the position of the source can be determined by triangulation from two measurement locations. The accelerometer 1709 may be configured to detect when the meter 1701 is turned on its side, thereby enabling the processor 1705 to allocate measurements to horizontal or vertical source angles accordingly. The accelerometer 1709 may also detect when the meter 1701 is moved or rotated quickly, thereby enabling the displayed icon 1713 to be erased until new data is accumulated. For example, when the meter 1701 is rotated or moved quickly, the processor 1705 may blank the displays 1703 and 1704 to avoid misleading the operator, or the displays 1703 and 1704 can be changed to show a busy-icon for example. Alternatively, the processor 1705 may be configured to correct the displayed icon 1713 according to the rotation measured by the accelerometer 1709 or the compass 1707. For example, the processor 1705 may subtract the measured rotation angle from the angle of the directional icon 1713, so that the icon 1713 continues to point toward the source after the rotation. In either case, as soon as sufficient additional detection data are acquired to enable an updated source angle determination, the displays 1703 and 1704 can be updated to again show an icon 1713 pointing toward the source.

In some embodiments, the meter 1701 may also include a microphone 1710, a sound generator such as a speaker 1711, and a hold button 1712. The microphone 1710 can enable the operator to record comments made during the inspection in real-time. The speaker 1711 can provide an acoustical alarm to warn the operator of a high radiation environment, and/or other alarms. The speaker 1711 can also provide special sounds indicating whether the source is to the right or left of the aiming plane, and yet another sound when the aiming plane is directly aligned with the source. The various sounds may be configured to indicate the magnitude of the source angle as well, for example being modulated or varied in amplitude or frequency or otherwise according to the size of the source angle, while also indicating which side the source is on, and further indicating when the system is directly aimed at the source. In this way the acoustical signal may assist the operator in localizing the source without looking away from the scene. The hold button 1712 may allow the operator to freeze the displays 1703 and 1704 with the accumulated radiation and directional information displayed, so that the operator can then read them at a later time. The hold button 1712 may be a press-to-run button, a press-to-hold button, a run-hold toggle switch, or other manually-operable control component. In a further embodiment, the holding and running modes may be controlled by spoken commands, such as the operator saying "hold" or "stop" to freeze the display, and "go" or "run" to resume updating the display by speaking one of the commands, which can be reliably discerned with low-cost microcontrollers in some embodiments.

The portable meter 1701 may be operated by a human operator, or by a robot operator with grasping means to manipulate the meter 1701. The robot may include viewing means to read the display 1703, or a wireless link to receive detection and angular data.

In some embodiments, the processor 1705 may continuously calculate the source angle relative to the current aiming plane, and then may update the icon 1713 to show the calculated source angle in real-time. The processor 1705 may be configured to update the source angle incrementally, with the oldest data being discarded or attenuated relative to the most recent acquisitions. Emphasis on the newest data may be accomplished using a ring buffer, or by weighting the most recent data above the older data, or by incremental averaging, or other means to reflect the latest angular results while discarding or attenuating the older results. Continuous updating of the calculated source location may help the operator to rapidly locate the source.

In some embodiments, the meter 1701 may be configured to determine when the aiming plane becomes aligned with the source. For example, the meter 1701 may use the "calculated angle" criterion to determine the alignment, wherein the aiming plane is aligned with the source when the calculated source angle is less than some threshold such as 1 degree or 2 degrees. Alternatively, the meter 1701 may use the "equal-rates" criterion, wherein the side detector rates are equal within expected statistical errors when the aiming plane and the source are aligned. As a further option, the meter 1701 may use a combination of the two criteria. Additionally, when the meter 1701 is aligned with the source, the display 1703 or 1704 may indicate that the aiming plane is aligned with the source using, for example, a special icon, thereby enabling the operator to localize the source more easily and more rapidly than possible with directional meters that fail to determine the magnitude of the source angle.

Embodiments of the meter 1701 may include a light beam transmitter 1725 emitting a light beam 1726. In some embodiments, the light beam 1726 may be directed along the aiming plane, thereby showing where the meter 1701 is aimed. In addition, the light beam 1726 may be configured to indicate the left or right direction toward the source, for example with an asymmetric beam shape such as a wedge pointing left or right. The beam shape may be further configured to indicate the magnitude of the source angle as well as the left-right direction, for example being elongated when the magnitude of the source angle is large or foreshortened when the source angle is small. In addition, the beam shape may be reduced to a circular spot, or caused to flicker, or otherwise visibly modulated, when the source angle is very small or zero, thereby indicating the exact source location visually when the meter 1701 is aligned with the source. Such a variable light beam shape, indicating the direction of the source as well as the magnitude of the source angle, greatly assists the operator in locating a source quickly without having to look away from the scene.

In another embodiment, the meter 1701 may be configured to redirect the light beam 1726 directly toward the calculated source location when determined. In some embodiments, the meter 1701 may be configured to rotate the light beam transmitter 1725 itself according to the calculated source angle. Alternatively, the meter 1701 may be configured to redirect the light beam 1726 using a rotatable mirror for example. In both cases, the redirected light beam 1726 may bathe the source location in light and thereby provide an unambiguous visual indication of the source location. The light beam 1726 may be flickered or modulated in shape or otherwise modulated to enhance visibility. When so directed toward the source, the light beam 1726 may appear to remain "locked on" to the calculated source location even as the meter 1701 is moved around and rotated. For example, the processor 1705 may be configured to detect any rotation of the meter 1701, using signals from the compass 1707 or otherwise, and thereby adjust the light beam 1726 direction accordingly to keep the light beam 1726 directed toward the source. In addition, the processor 1705 may be configured to recalculate the source angle repeatedly and to adjust the light beam 1726 angle in near-real-time. By these means, the processor 1705 may cause the light beam 1726 to remain continuously and persistently directed toward the source location, thereby revealing the source to the operator in a compelling and intuitive visual manner.

Embodiments of the meter 1701 may include a camera 1727 or other imaging device configured to record images of the scene. The camera 1727 may be aligned with the aiming plane, in which case an icon or other indicator may be added to the image at the calculated source location. In addition to recording the scene and the source location, the camera 1727 may also be useful for determining a rotation angle of the meter 1701. For example, as the meter 1701 is rotated to different orientations, the image shifts accordingly, and the processor 1705 can then perform image analysis by comparing sequential images, and thereby determine how far the meter 1701 has been rotated. The processor 1705 can then use that rotation angle, along with the detector counting rates acquired both before and after the rotation, to localize the source using, for example, interpolation.

In an alternative embodiment, the system 1701 may be configured to redirect the image so that it is centered on the source location. For example, the system 1701 may be configured to rotate the camera 1727 according to the calculated source angle. Alternatively, the system 1701 may use a rotating mirror, or other optical means, to cause the image to be centered on the calculated source location. In addition, the camera 1727 may be configured to vary a zoom lens or equivalent, and thereby acquire both wide-angle and magnified images centered on the source location. For example, the image scene (centered on the calculated source location) may be magnified successively in various images, such as acquiring a new image whenever the angular uncertainty in the source angle is improved with further data. In addition, the angular uncertainty may be indicated on each image by a numerical or graphical overlay for example. The camera 1727 may be activated upon the start or end of each period of detector data acquisition, or manually by an operator, or continuously, or periodically, or upon a computer command, or whenever the meter 1701 is rotated, or otherwise.

In some embodiments, the meter 1701 may be configured to accumulate detector data for a particular time interval termed the "integration time," and then may analyze the accumulated data to determine the source angle. For example, the integration time may be set to a default value such as one second or ten seconds, or it may be adjustable manually by the operator using an integration time control 1728 such as a knob, or the integration time may be adjusted automatically by the processor 1705. A short integration time may be sufficient to localize the source quickly if the radiation level is high, but if the source is small or well-shielded, the rates are likely to be much lower or barely above background, in which case a longer integration time may be preferable. As a further option, the integration time may be adjusted dynamically in real-time according to the detection rate obtained, or according to the angular uncertainty so far obtained, or other criteria. The processor 1705 may be configured to perform a method including first checking the overall radiation level, for example by checking the accumulated counts in the middle detector and/or by adding the counting rates of the two side detectors. The processor 1705 may be configured to then adjust the integration time according to the criteria, such as a sufficient time to obtain sufficient counts for a satisfactory determination of the source angle.

In another embodiment, the processor 1705 may be configured to follow a sequential acquisition program that includes first acquiring detector data for a short integration time, then obtaining an early indication of the presence of a source based on the sum of the side detector rates being above background levels, then continuing to acquire data for a second integration time to obtain sufficient data to determine the sign of the source angle based on the difference between the two side detector counting rates, then continuing to acquire data for a third integration time to obtain sufficient data to determine the magnitude of the source angle based on a comparison of the middle detector and side detector rates, and then acquiring data for a fourth integration time to obtain sufficient data to reduce the uncertainty in the source angle to a predetermined level.

In some embodiments, the processor 1705 may be configured to analyze the detector data and calculate a best-fit source angle continuously while further data is being accumulated. The processor 1705 may be configured to update the source angle determination after every detection, or at preset intervals such as once per second, using whatever data has been accumulated so far. In one embodiment, the processor 1705 may be configured to determine when the meter 1701 has been rotated, and to then delete the accumulated detector data, and to then start over with new data, thereby avoiding showing an outdated result to the operator. In a second embodiment, the processor 1705 may be configured to determine how far the meter 1701 has been rotated, and then subtract that rotation from the current estimate of the source angle before continuing to accumulate further detection data, thereby continuing to provide the best estimate of the source angle to the operator throughout the rotation.

Figure 17B:
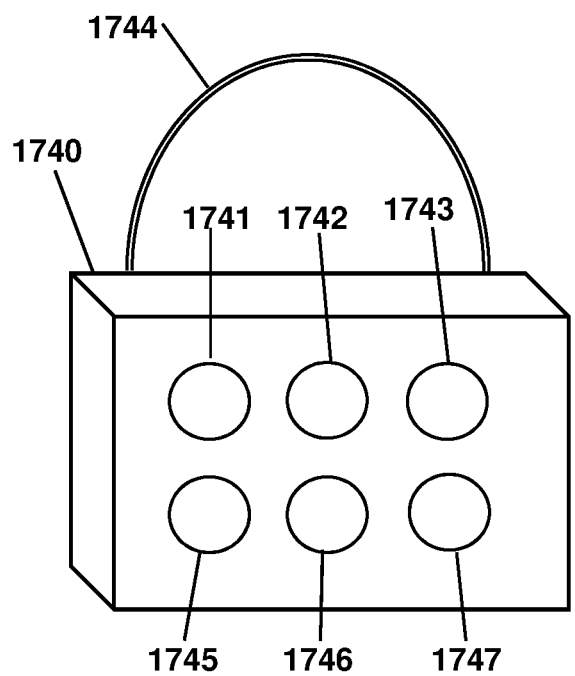
FIG. 17B is a perspective sketch of an exemplary wearable health and safety monitor according to some embodiments.

FIG. 17B is an exemplary sketch in perspective of a wearable health and safety monitor 1740 which may be worn by the operator of the portable meter 1701 of FIG. 17A. The monitor 1740 may be wirelessly linked to the meter 1701, using Bluetooth or Wi-Fi or other communication technology for example. Embodiments of the monitor 1740 can be worn by the operator using an attachment 1744 such as a belt clip, harness, neck strap, or the like. The monitor 1740 can continuously monitor the health and safety status of the operator, and can communicate any detected problems automatically to the meter 1701, which can pass the alarm to a central facility and/or peer nodes in the LAN. Alternatively, the monitor 1740 may transmit the alarm directly to an external receiver such as an emergency response facility. The monitor 1740 may include a 3-axis accelerometer 1741 or other means to determine whether the operator remains upright or has fallen, a microphone 1742 configured to receive verbal data from the operator, and a wireless transceiver 1743 configured to communicate with the processor 1705 or other receiver. The monitor 1740 may further include biometric devices such as a respiration sensor 1745, a pulse timer 1746, and a blood pressure sensor 1747 as well as other health and safety related diagnostics. Thus, the meter 1701, with its linked health and safety monitor 1740, can enable a near-instantaneous rescue response when the operator experiences an emergency situation in the field, according to some embodiments.

Figure 17C:
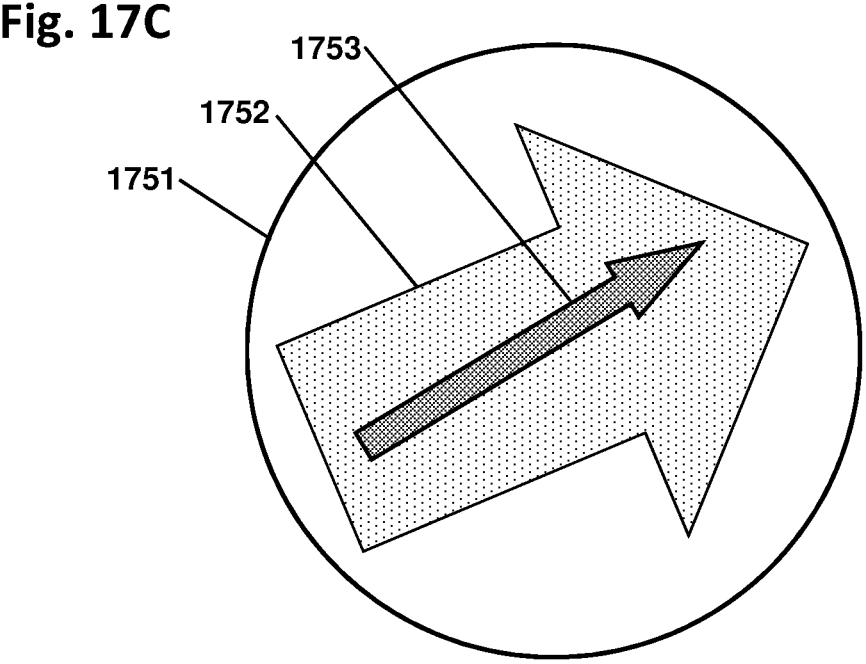
FIG. 17C is a perspective sketch of an exemplary display showing two analysis results according to some embodiments.

FIG. 17C shows an exemplary embodiment of a display 1751 configured to provide information about the source angle as well as the uncertainty in the source angle. In some embodiments, the processor 1705 of FIG. 17A may be configured to execute two parallel analyses with two different integration times. For example, the processor 1705 may be configured to carry out a first analysis using a short integration time, which thereby provides a rapidly updated value of the source angle, albeit with large uncertainties due to the limited number of detections observable in that short integration time. The processor 1705 may be further configured to carry out a second analysis concurrently, using a much longer integration time, which thereby provides a more reliable measure of the source angle, but more slowly. Both the fast and slow results may be displayed and updated continuously, or periodically, so that the operator can assess the results visually in real time. For example, the fast results with lower resolution may be displayed using a broad directional icon 1752, thereby suggesting a general source direction with a relatively wide range of angles, overlain by a sharper and more stable directional icon 1753 showing the slower, high-resolution angle result. With such a composite display, the operator can evaluate the source location in real-time while moving through a clutter field and other variations, by attending either the fast low-resolution icon 1752 or the slow high-resolution icon 1753 according to the current inspection conditions.

Figure 18A:
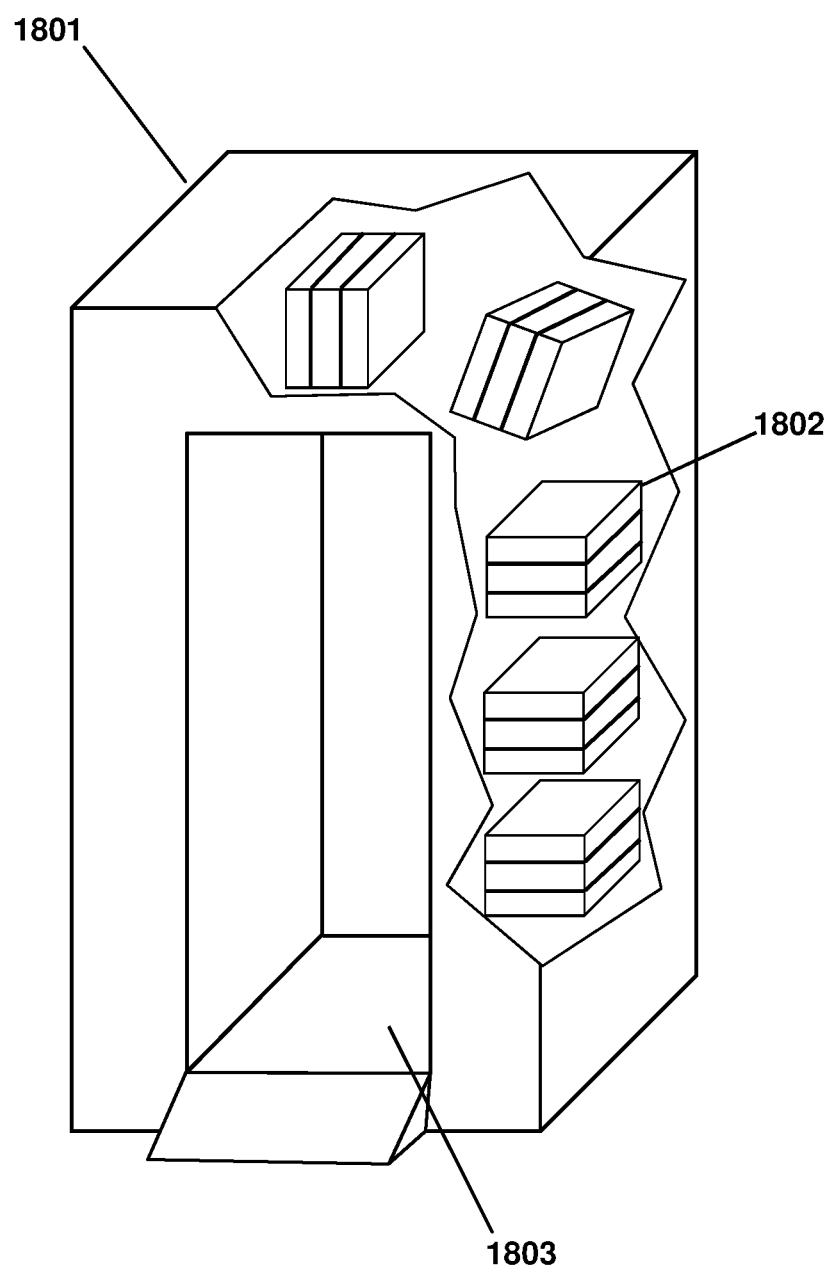
FIG. 18A is a sketch in perspective, partly cut-away, of an exemplary walk-through portal with multiple copies of the system arranged in the walls of the portal according to some embodiments.

FIG. 18A shows in perspective, partially cut-away, an exemplary embodiment of a walk-through portal 1801 in which a plurality of the present systems 1802 are mounted. In this application, it may be advantageous to mount the systems 1802 with their aiming planes horizontal so that each system 1802 can measure the vertical location of the source on a person. Systems 1802 may be mounted in the walls and ceiling of the portal 1801. In another embodiment, further systems 1802 may be mounted under the floor 1803 of the portal 1801 as well. Alternatively, the floor 1803 may include an automatic weighing scale configured to determine when a person is in the portal 1801, and to sound an alarm if the person tries to pass through the portal 1801 too quickly. By localizing the source, the portal 1801 can indicate where the source is concealed on a worker's clothes, toolbox, hair, shoes, etc., according to some embodiments.

Figure 18B:
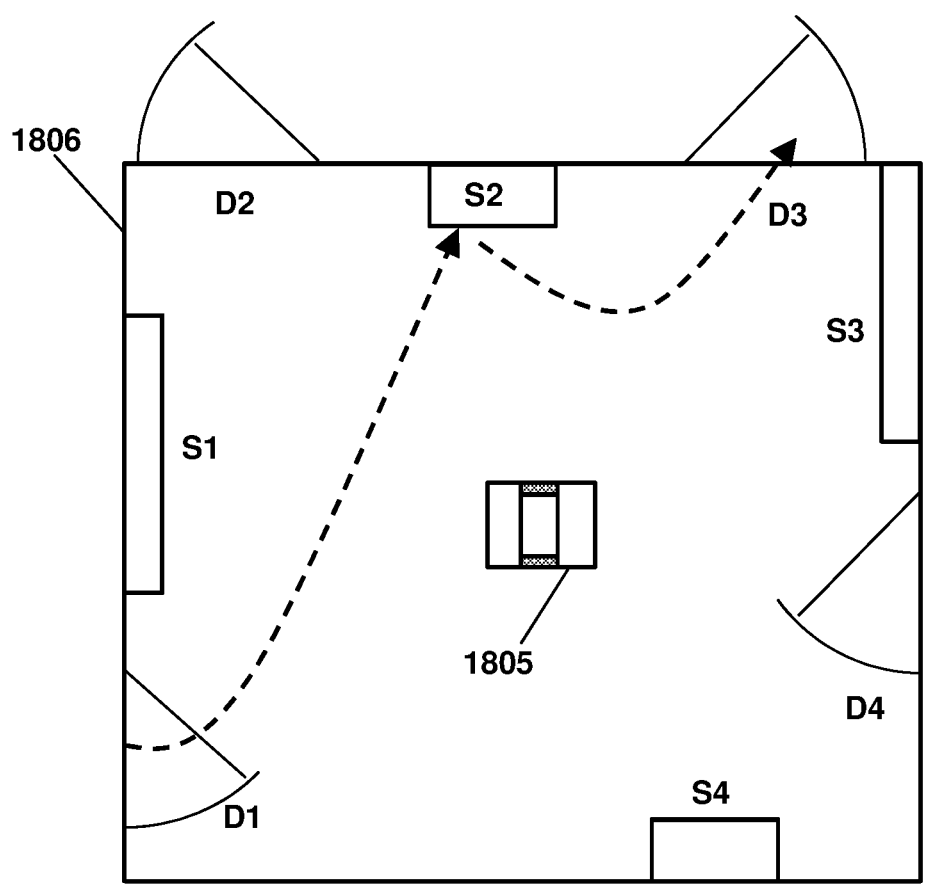
FIG. 18B is a sketch of a room or passageway containing an exemplary directional monitoring system according to some embodiments.

FIG. 18B is a top-view sketch of a room or other passageway 1806 containing an exemplary embodiment of a double-sided directional system 1805, such as those of FIG. 11, 13, or 14. The system 1805 may be mounted in the ceiling or above the floor or otherwise configured to measure and record the motions of radioactive sources throughout the room 1806. Four doors (D1-D4) and four shelves (S1-S4) are also in the room 1806. In a radiation contamination event, a staff member unknowingly carried a contaminated radioactive tool in through door D1, picked up something from shelf S2, and then left through door D3 as indicated by dashed arrows. The system 1805 can detect the source, measure its motions including direction and velocity at each position, and record the event in real-time. The data may assist inspectors in determining how the contamination was spread, where it came from, and where it went to, all of which would be impossible with a non-directional detector.

Figure 19A:
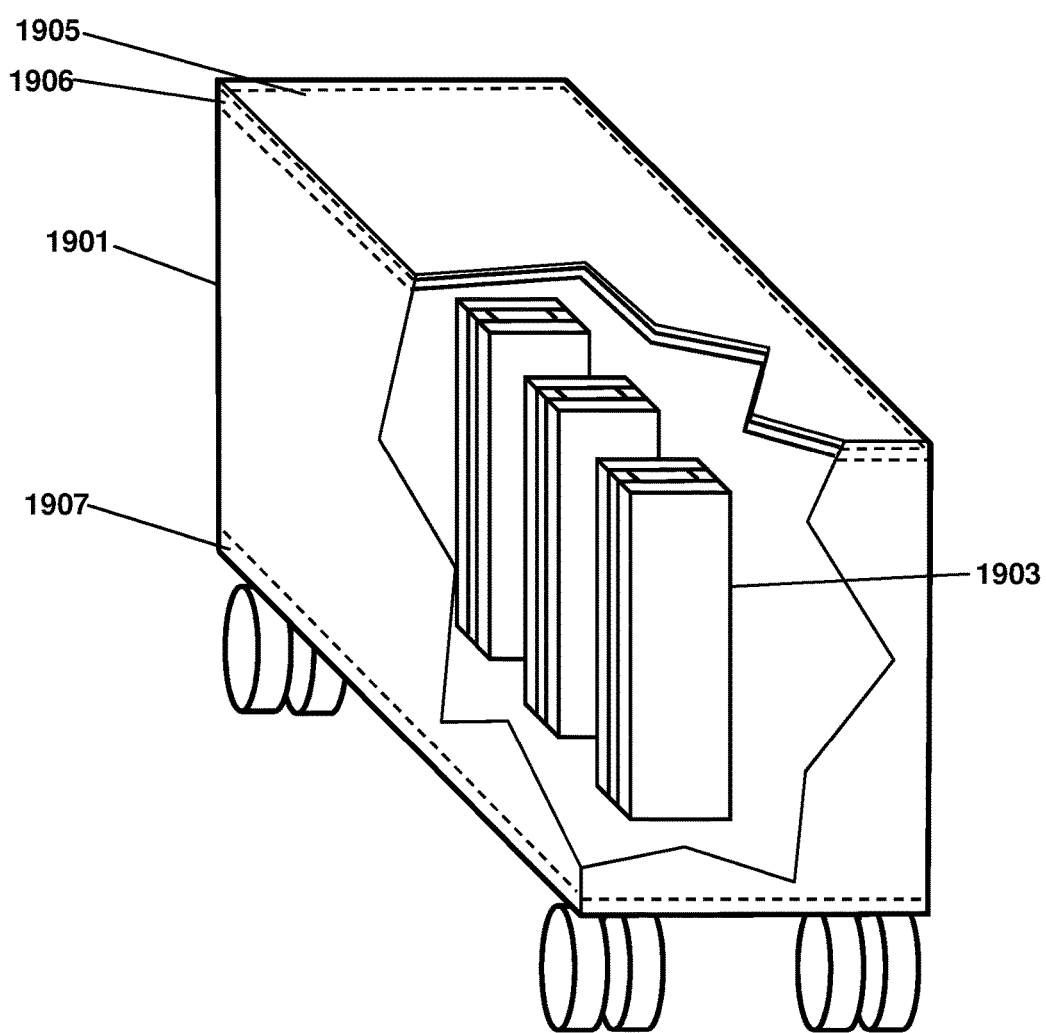
FIG. 19A is a sketch in perspective, partly cut-away, of an exemplary mobile radiation scanner containing multiple copies of the system according to some embodiments.

FIG. 19A shows in perspective an exemplary embodiment of a mobile radiation scanner 1901 comprising a trailer or van configured to detect hidden sources in, for example, an urban environment. The mobile scanner 1901, partially cut-away, may include an array of the present systems 1903. Preferably the array of systems 1903 nearly fills the central region of the mobile scanner 1901 so as to maximize the detection area when viewed from the side. The systems 1903 may be of the bidirectional type as depicted in FIGS. 11, 13 and 14, to detect particles arriving from either the left or right side of the mobile scanner 1901. Alternatively, the systems 1903 may be of the unidirectional type as depicted in FIG. 1 to detect particles arriving from one side, such as the curb side, of the mobile scanner 1901.

Some embodiments may also include a cosmic ray veto counter 1905, comprising a plastic scintillator for example, configured to reject events that include a cosmic ray signal. An optional neutron shield 1906 may also be added to the ceiling to block naturally occurring low-energy neutrons, and a second neutron shield 1907 may be mounted on the floor to block ground-effect neutrons. The neutron shields 1906 and 1907 may each include a layer of LiF in HDPE, for example.

In some embodiments, the detection rates and directionality results of each of the systems 1903 may be recorded as well as the GPS coordinates and bearing. From that data, the mobile scanner 1901 or a base computer can prepare a two-dimensional map of radiation sources in the environment. High sensitivity and high specificity can be achieved in the radiation map due to the directionality of each system 1903. Any future changes to the radiation distribution would then be a cause for alarm.

In some embodiments, some of the systems 1903 may include neutron-sensitive gamma-blind detector material, while others may include gamma-sensitive neutron-blind material, thereby simultaneously providing a map of the neutron radiation distribution and a separate map of gamma sources. Likewise the systems 1903 may be configured to detect high energy neutrons and to reject low energy neutrons, or vice-versa. Most naturally-occurring background neutrons have low energy due to multiple scattering in the atmosphere, whereas neutrons from weapon materials generally have a higher energy of 1 MeV to a few MeV depending on composition. In some embodiments, detecting even a few high energy neutrons would be suspicious, particularly if they all come from a particular location.

Figure 19B:
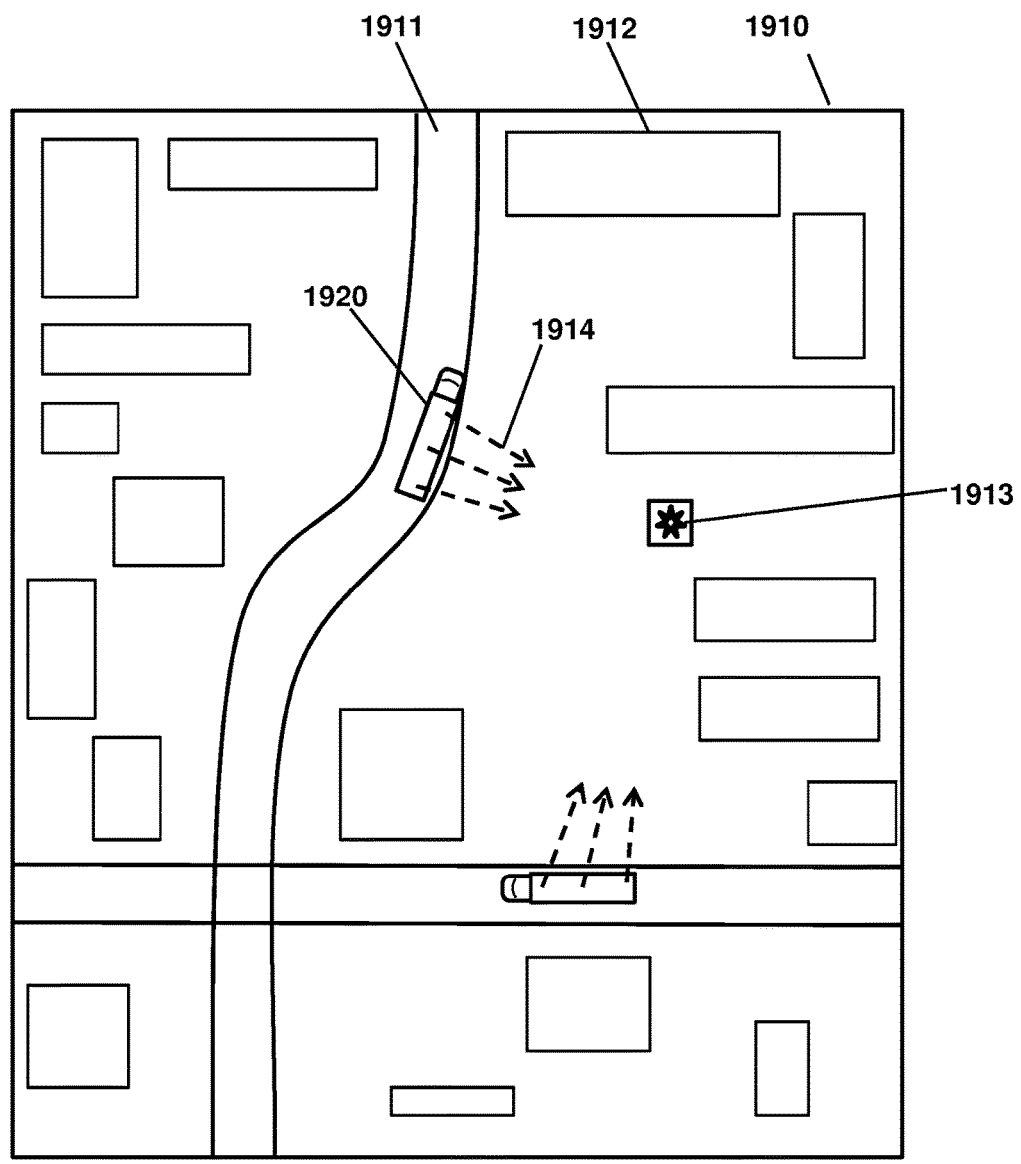
FIG. 19B is a notional sketch of an urban region being scanned by exemplary directional detectors, according to some embodiments.

FIG. 19B is a notional sketch of a map 1910 including roads 1911 and buildings 1912. A mobile scanner 1920 such as that of FIG. 19A drives along the roads 1911 and measures radiation coming from a clandestine weapon 1913 and determines the source direction as indicated by dashed arrows 1914. Two positions are shown. The clandestine weapon 1913 is thereby detected and localized.

Figure 20:
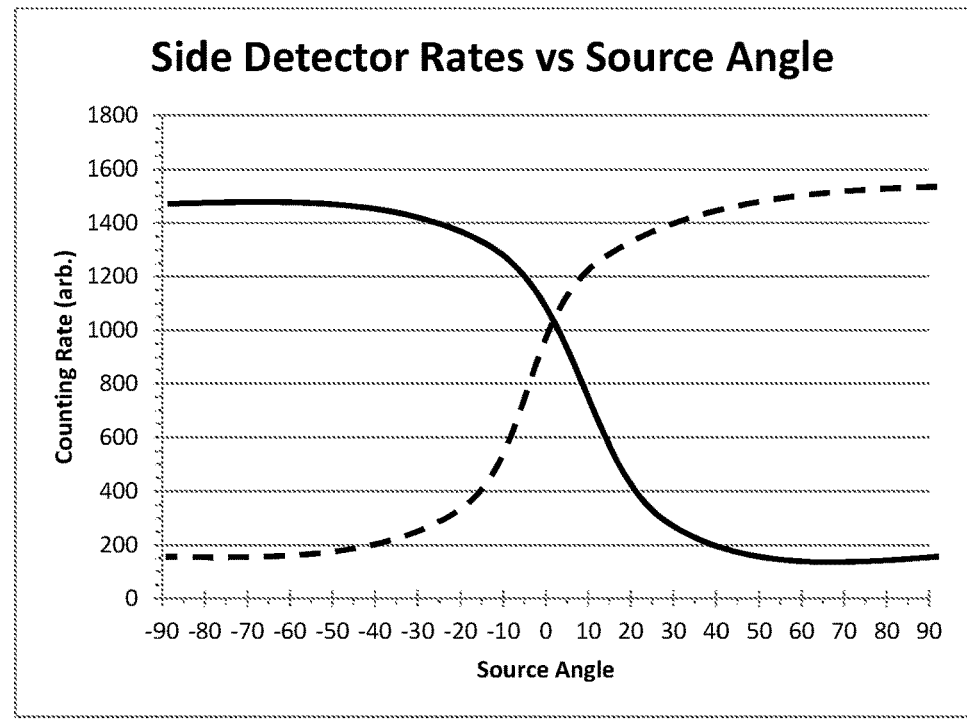
FIG. 20 is a graph showing counting rates of the two side detectors versus the source angle, according to some embodiments.

FIG. 20 is a graph showing schematically the side detector detection distributions versus the angle of a source. The curve shown in dash is the expected counting rate in arbitrary units, for one of the side detectors. It exhibits a high counting rate when the source is at +90 degrees, and drops to a low counting rate when the source moves around to −90 degrees relative to the aiming plane. This is expected since the opposite side detector partially blocks the gammas from reaching that side detector when the source is on the opposite side. The other side detector shows a high rate when the source is at −90 degrees, and a low rate at +90 degrees for the same reason.

Figure 21:
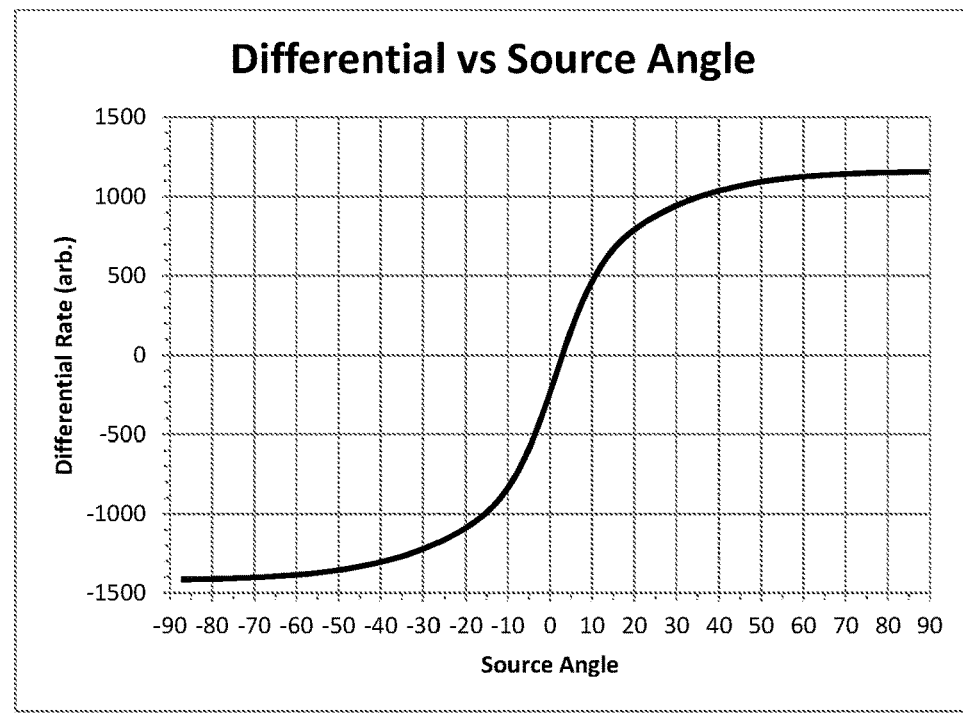
FIG. 21 is a graph showing the differential versus source angle, according to some embodiments.

FIG. 21 is a graph showing schematically the differential between the two side detector counting rates for the case of FIG. 20. The differential equals the counting rate of the first side detector minus the second side detector rate. The differential curve is a smooth antisymmetric distribution centered on the aiming plane at zero degrees.

Figure 22:
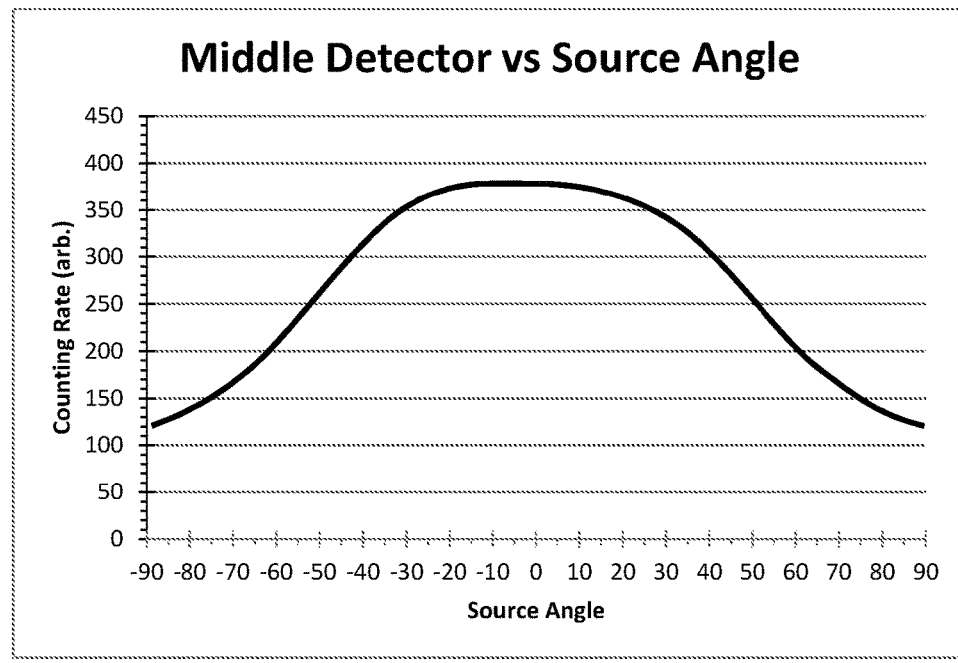
FIG. 22 is a graph showing the counting rate of the middle detector versus the source angle, according to some embodiments.

FIG. 22 is a graph showing schematically the counting rate for the middle detector versus source angle. The curve shows the middle detector with a high detection rate when the system was aimed at the source.

Figure 23:
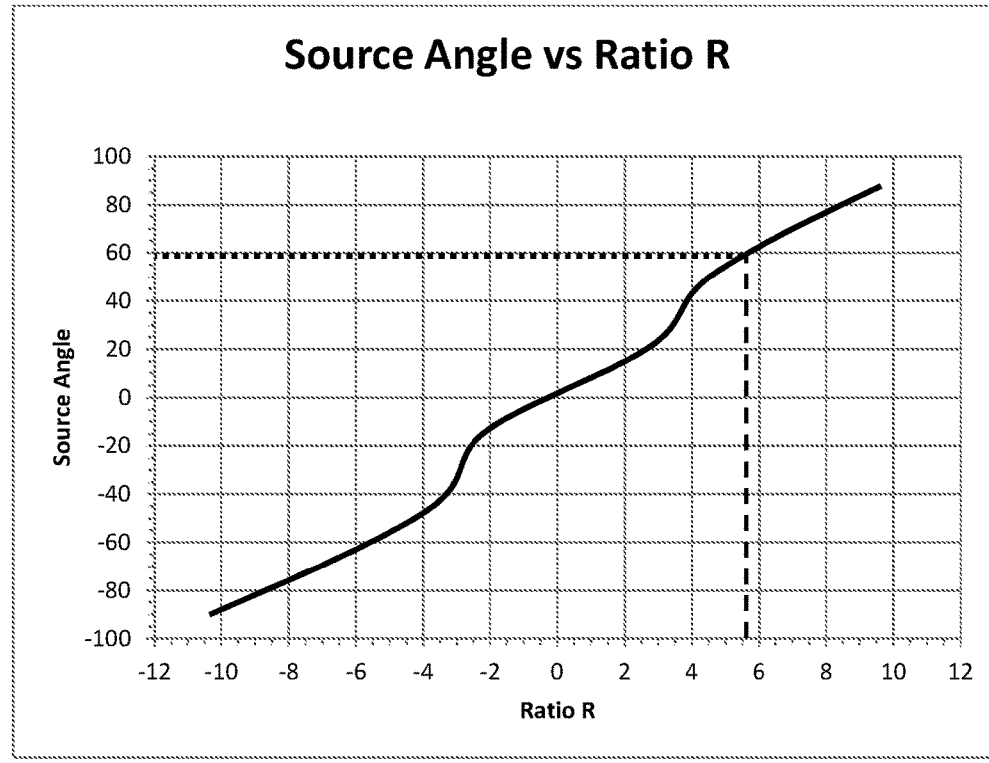
FIG. 23 is a graph showing the angular correlation function that relates the source angle to the counting rate ratio, according to some embodiments.

FIG. 23 is a graph showing schematically the angular correlation function, derived from the detection data versus source angle. The curve of FIG. 23 is the angular correlation function relating the source angle to the ratio R=D/S3 where D is the differential between the two side detector counting rates as shown in FIG. 21, and S3 is the middle detector counting rate of FIG. 22. The angular sensitivities of the side detectors and the middle detector are sufficiently different that the function graphed can determine the source angle, both sign and magnitude, from a single set of detector rates.

In operation, according to some embodiments, the counting rates may be acquired, and the differential may be found by subtracting the counting rate of the first side detector from the second side detector. The differential may be divided by the middle detector rate, thereby obtaining the ratio R. Reading across the horizontal axis of FIG. 23 to the calculated value of R, the curve value at that point may indicate the corresponding source angle on the vertical axis.

The correlation is monotonic, meaning that a unique source angle can be found from R. For example, using the angular correlation function of FIG. 23, the simulated detection data with a ratio of R=5.6 (dashed line) corresponds to a source angle of about 59 degrees (dotted horizontal line).

Figure 24:
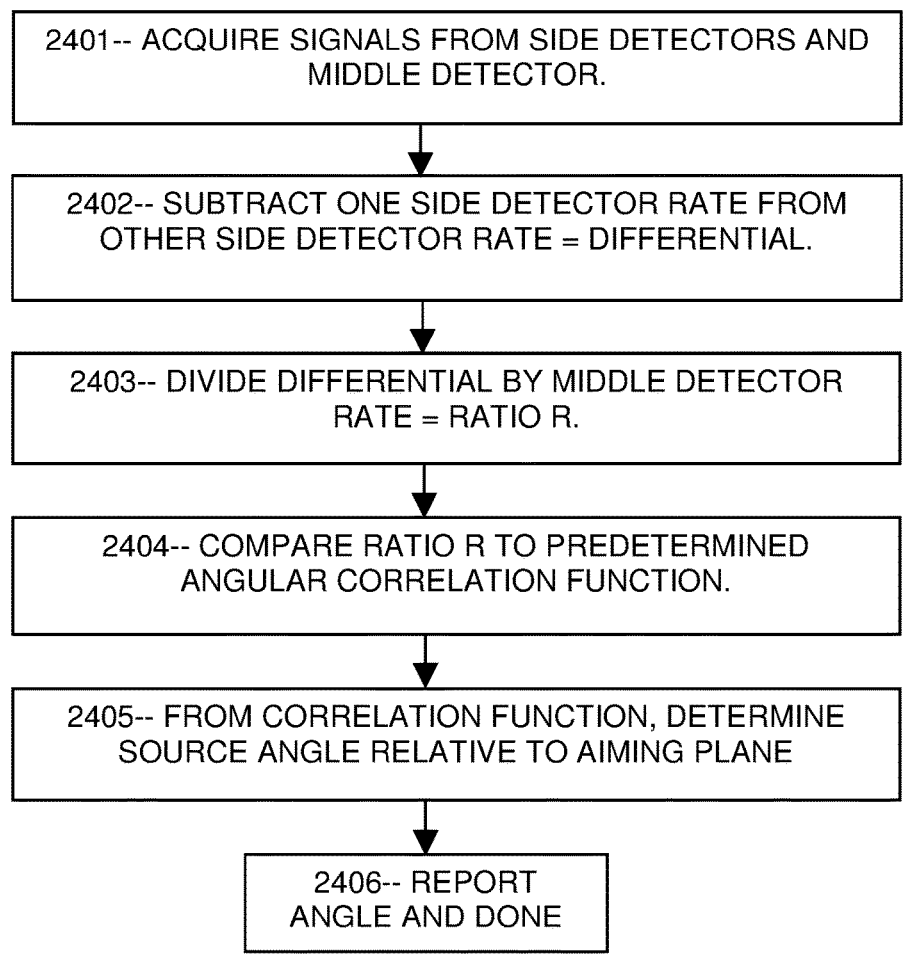
FIG. 24 is a flowchart showing an exemplary method for calculating the source angle according to some embodiments.

FIG. 24 is a flowchart showing an exemplary method for determining the source angle according to some embodiments. At 2401 the side detector counting rates and the middle detector counting rates may be measured. At 2402 the detection rates for one side detector may be subtracted from the other side detector, thereby obtaining a differential. The ratio R may be calculated 2403 by dividing the differential by the middle detector rate. R may be compared 2404 to the predetermined angular correlation function, and the source angle may be determined 2405 as the particular angle that matches the angular correlation function at the calculated value of R. At 2406 the calculated angle, both sign and magnitude, may be displayed or transmitted or otherwise reported.

More specifically, the system may include non-transient computer-readable media containing instructions that, when executed by a computer or processor, carry out a method to determine the source angle from detection data. The method may include measuring detection rates S1 and S2 of the side detectors and S3 if the middle detector, calculating a differential D equal to the difference between the side detector counting rates or D=S1−S2, and dividing the differential by the middle detector counting rate to obtain a ratio R=D/S3. Alternatively and equivalently, the side detector rates may be divided by the middle detector rate first and then subtracted, as in R=(S1/S3)−(S2/S3). The method may include comparing R (or its inverse) to the predetermined angular correlation function. Or, equivalently, the value of R may be provided as input to the predetermined angular correlation function. Since the correlation function is configured to relate the source angle to the particle detection rates (or to the ratio R), the angular correlation function may thereby provide the value of the source angle as output. The method may include determining both the sign and magnitude of the source angle from the comparing of R to the angular correlation function, thereby directly obtaining the angle between the source direction and the aiming plane. Positive and negative values of the differential may correspond to positive and negative values of the source angle respectively, while large and small magnitudes of the ratio may correspond to large and small magnitudes of the source angle. Preferably, the counting rates of each detector may be corrected for the detection efficiency and normal background rate of each detector before the differential is calculated. In one embodiment, the analysis may use a different measure of the detector activity, other than the counting rates, such as the integrated signal current or the accumulated charge from each detector, or other measure associated with particle detection in each detector, so long as the resulting ratio is related to the source angle by a specific, and preferably monotonic, relationship.

Figure 25:
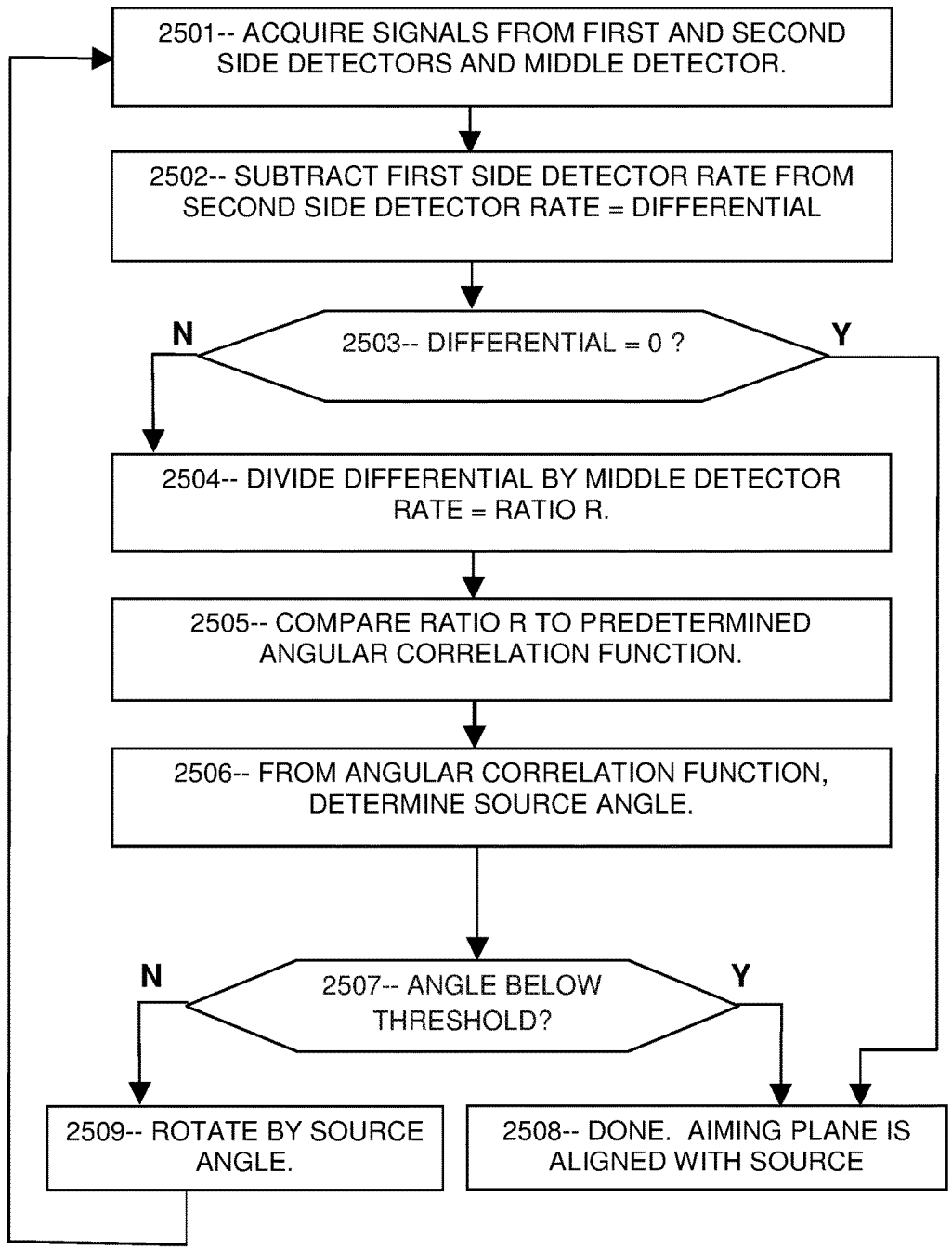
FIG. 25 is a flowchart showing an exemplary method to rotate the system into alignment with the source according to some embodiments.

FIG. 25 is a flowchart showing an exemplary method for aligning the system with the source. Many applications require that the system be rotated into alignment with the source to localize the source more precisely, or to acquire spectral data on the source using an energy-resolving fourth detector positioned between the shields for example, or for other reasons. To align the aiming plane with the source location, the side detector counting rates and the middle detector counting rates may be measured 2501. At 2502 the detection rates for one side detector may be subtracted from the other side detector, thereby obtaining a differential. At 2503 the differential may be tested for being at zero or within some limit of zero. If so, the task is done 2508, since the aiming plane is aligned with the source. If the aiming plane is not yet aligned with the source, the ratio R may be calculated 2504 by dividing the differential by the middle detector rate. R may be compared 2505 to the predetermined angular correlation function, and the source angle may be determined 2506 as the particular angle that matches the angular correlation function at the calculated value of R. At 2507, if the magnitude of the calculated angle is below a threshold value, the aiming plane is sufficiently aligned with the source 2508 and the task is done. If the calculated angle is not below the threshold value, then 2509 the system may be rotated according to the calculated angle, including both sign and magnitude of the calculated angle, thereby bringing the aiming plane closer into alignment with the source. The method then returns to the beginning 2501 to acquire detection data at the new orientation.

In some embodiments, the system can arrive at, or close to, the source location in a single rotation according to the calculated source angle. Preferred embodiments can then verify the alignment by comparing the side detector counting rates, which are substantially identical (within statistical uncertainties) when the source is aligned with the aiming plane. By determining the magnitude of the source angle as well as its sign, embodiments of the system can avoid the time-consuming, error-prone, skill-intensive, iterative hunt-and-peck process employed by conventional detectors to locate a source.

Figure 26:
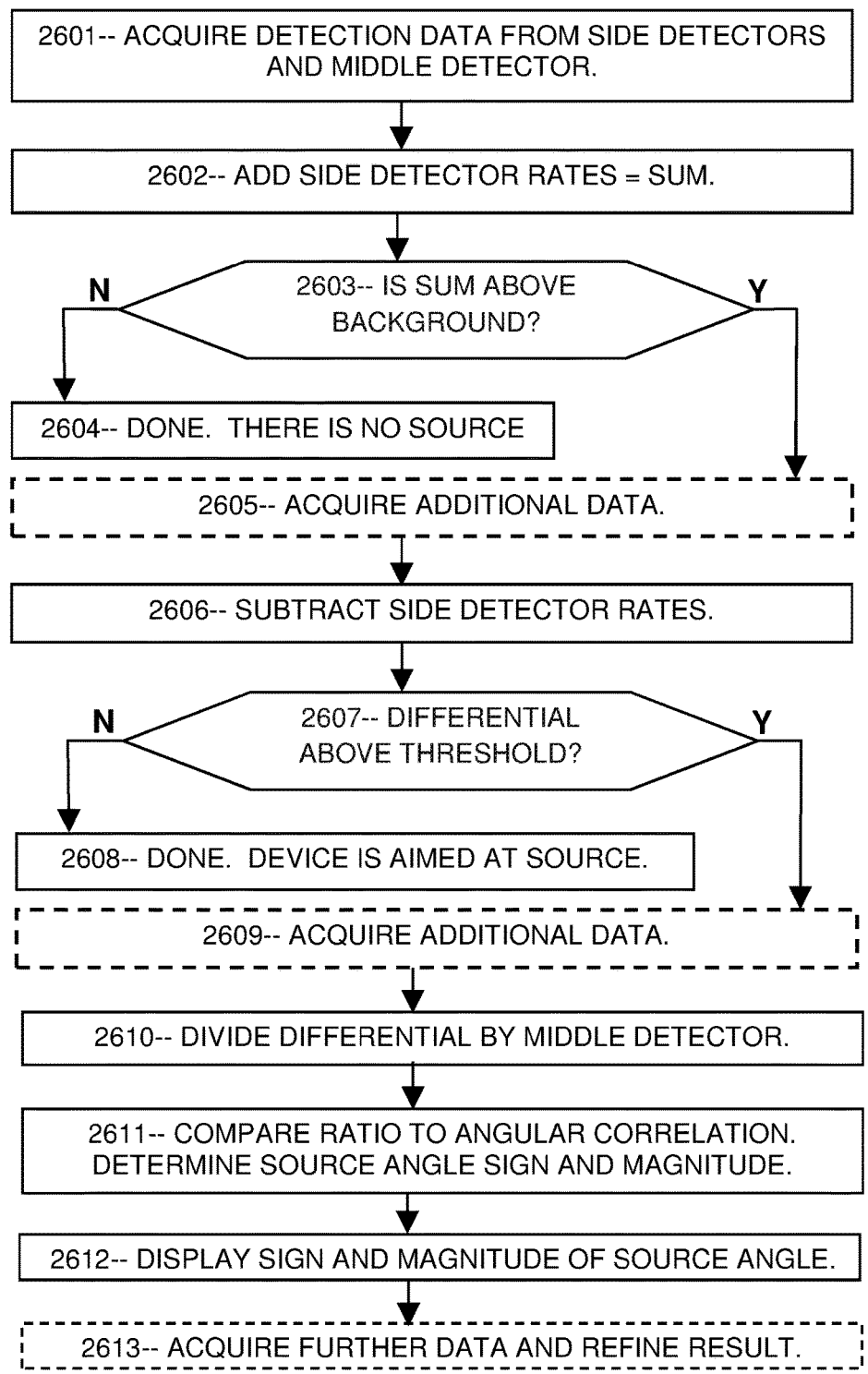
FIG. 26 is a flowchart showing an exemplary staged analysis method to optimize the use of low detection rates according to some embodiments.

FIG. 26 is a flowchart showing an exemplary method for determining the source angle in incremental stages according to some embodiments. In this method, successive details of the source location are revealed sequentially, each detail being obtained with an additional set of detector data. The simplest results are obtained first, then the full source location is determined at the end. At 2601, signals may be acquired from the side detectors and the middle detector during a first integration time, and counting rates may be calculated. At 2602, the side detector rates may be added and the sum compared 2603 to a normal background rate. If the summed signals are not significantly above background levels, the system may indicate 2604 that no source is present, or at least no source is yet detected. But if the sum of the side detector rates is above the normal backgrounds, then a source is known to be present, although its location is not yet determined. In that case, additional data may be acquired 2605 in a second integration period to enable a more reliable angular analysis. At 2606, the differential may be calculated by subtracting one of the side detector rates from the other, and the differential may be compared 2607 to a predetermined threshold. If the differential is small or below a threshold, the task is done 2608 since the aiming plane is now aligned with the source. If the differential is not zero, or is not below a predetermined threshold, then additional detector data may then be acquired 2609 during a third integration time, to accumulate sufficient counts in the middle detector. For example, additional data may be required if the middle detector counting rate is still comparable to its statistical uncertainty, since in that case there are not enough middle detector counts to determine the magnitude of the source angle. After such additional acquisition, if necessary, the source angle may be calculated by dividing the differential by the middle detector rate 2610 and comparing the ratio to the predetermined angular correlation function 2611. The source location or source angle may be reported 2612 by displaying it on a screen, transmitting it to a facility computer, storing it in media, or otherwise responding according to the application needs.

Optionally 2613 a fourth acquisition interval may be added to acquire sufficient data to reduce the angular uncertainty in the result. If a source is present, it is usually worth taking some extra data to obtain the best angle determination.

According to some embodiments, the predetermined angular correlation function may be a table of detection ratios versus source angle. The table values can be linearly interpolated whenever an intermediate value is needed between the table entries. The system can determine the sign of the source angle from the sign of the difference between the counting rates of the two side detectors, and can determine the magnitude of the source angle from the counting rate in the middle detector according to the predetermined angular correlation function.

Figure 27:
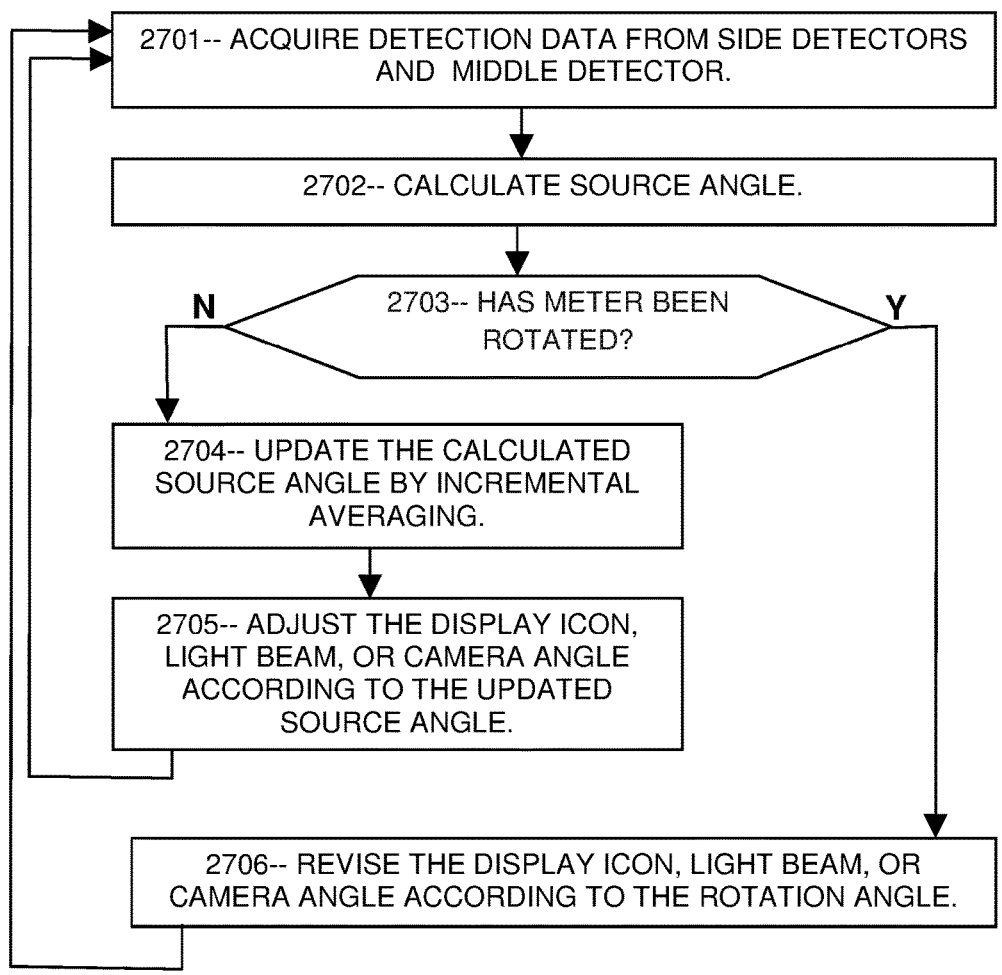
FIG. 27 is a flowchart showing an exemplary method to update the calculated source angle, according to some embodiments.

FIG. 27 is a flowchart of an exemplary method to continuously or periodically update the source angle as conditions change, thereby causing the light beam or camera view or displayed icon to remain persistently aimed at the source location even as the system is rotated. The method of FIG. 27 may be particularly applicable to a portable radiation survey meter such as that disclosed in FIG. 17. At 2701, detection data may be acquired from the side and middle detectors. At 2702 a calculated source angle value may be determined from the detection data, using the angular correlation method for example. At 2703 the meter orientation may be checked to determine if the system has been rotated. This step may involve signals from a compass or accelerometer configured to sense rotations, or it may involve image processing to detect a change in direction, or other means for determining if the system has been rotated and by how much. If no such rotation is detected, then 2704 the source angle may be updated by combining the currently calculated value with the previously determined source angle results, so as to obtain a new value that reflects both the recent measurement and the past data. In some embodiments, combining the old and new data may include discarding or otherwise attenuating the oldest data while emphasizing the more recent results. For example, the processor may be configured to store sequential calculated values of the source angle in a ring buffer, such that each newest result overwrites the oldest value in the buffer, and then the entire set of values may be averaged to obtain a best-fit or maximum likelihood or time-average value of the source angle. Alternatively, the current result may be averaged incrementally with the prior average, wherein the current result and the prior average are weighted to obtain an updated average source angle. For example, in a particular embodiment, an updated average may be calculated by adding the old average times 0.9, plus the new value times 0.1. The resulting updated average thereby incorporates the new results incrementally into the running average while gradually attenuating the oldest measurements. At 2705, using the updated average source angle so obtained, the system may redirect a light beam, and/or reorient the view of a camera, and/or redisplay a directional icon pointing toward the source according to the updated average source angle. If, on the other hand, the meter has been found to be rotated, then 2706 the display icon and/or light beam and/or camera angle may be revised according to the rotation angle (that is, adjusted opposite to the rotation angle), thereby causing the light beam or camera or icon to continue pointing toward the source location after the rotation. Thus the light beam or camera or icon may be adjusted according to the updated source angle if the system is not rotated, and if the system is rotated the items may be adjusted opposite to the rotation angle, so as to persistently remain centered on the source location. In addition, according to the exemplary flowchart, whenever such a rotation occurs, the most recent detection data may be discarded, since there is no way to know what orientation of the meter corresponded to while the meter was being rotated. In every case, the flow returns to the initial step 2701 of acquiring additional data. By causing the light beam or camera view or display icon to remain persistently locked onto the source location, while the source angle is repeatedly refined and while the meter is arbitrarily rotated, the system greatly assists operators in finding the source.

Embodiments of the system as described herein can provide many advantages over conventional detectors. (a) Embodiments can determine the full sign and magnitude of the angle between the aiming plane and the source direction. (b) Embodiments can determine the source angle from a single set of detector data without rotations or iteration. (c) In applications requiring that the system be aimed at the source, embodiments of the system can be rotated according to the calculated angle and thereby converge on the source direction in only one rotation. (d) Embodiments can achieve high detection efficiency because the detectors, unobstructed by shields or collimators, have an open view of the source particles regardless of the orientation of the system. (e) Embodiments of the system can be compact, light-weight, low-cost, easy to use in an inspection environment, suitable for a variety of important security scanning applications, and virtually immune to defeat by conventional shielding or obfuscation techniques.

For many applications in radiation detection, the ability to localize a lost or clandestine radioactive source is enabling. Advanced radiation detection systems like those disclosed herein will be needed in the coming decades to protect innocent people from the threat of nuclear and radiological terrorism.

The embodiments and examples provided herein illustrate the principles of the invention and its practical application, thereby enabling one of ordinary skill in the art to best utilize the invention. Many other variations and modifications and other uses will become apparent to those skilled in the art, without departing from the scope of the invention, which is defined by the appended claims.

What is claimed is:

1. A system for detection and localization of a radioactive source, comprising:
   two side detectors, separated by a predetermined distance and oriented parallel to a centrally positioned aiming plane, wherein each side detector is configured to emit signals upon detecting particles from the source, and to block at least 50% of the particles orthogonally incident thereon;
   a middle detector positioned at least partially between the side detectors, wherein the middle detector is positioned closer to the front of the system than the back of the system and configured to emit signals upon detecting particles from the source; and
   a processor configured to calculate, based at least in part upon the signals, the angle of the source location relative to the aiming plane.

2. The system of claim 1, wherein the system includes no passive shields or collimators.

3. The system of claim 1, wherein the width of the middle detector is at least four times the thickness of the middle detector, and the middle detector is oriented perpendicular to the aiming plane.

4. The system of claim 1, wherein the width of the middle detector is at least 2 times the average interaction distance of the particles therein, and the thickness of the middle detector is at most 0.5 times the average interaction distance of the particles therein, and the middle detector is oriented perpendicular to the aiming plane.

5. The system of claim 1, further comprising a shield slug configured to block most particles incident orthogonally thereon and positioned between the side detectors and behind the middle detector.

6. The system of claim 1, wherein one of the side detectors is configured to emit a first signal, the other side detector is configured to emit a second signal different from the first signal, and the middle detector is configured to emit a third signal different from the first and second signals.

7. The system of claim 1, further comprising a rear-facing detector configured to emit signals upon detecting particles from the radioactive source, wherein the rear-facing detector is slab-shaped, oriented perpendicular to the aiming plane, and positioned closer to the back than the front of the system.

8. The system of claim 1, wherein the middle detector is one of a plurality of middle detectors, wherein each middle detector of the plurality is slab-shaped, positioned between the side detectors, closer to the front of the system than the back of the system, and oriented perpendicular to the aiming plane, and wherein each middle detector of the plurality is configured to emit signals upon detecting particles from the radioactive source.

9. The system of claim 1, further comprising a fourth detector positioned between the side detectors and behind the middle detector, wherein the fourth detector is configured to measure the energies of the particles with an energy uncertainty of at most 10%.

10. The system of claim 1, further comprising a fourth detector positioned between the side detectors and behind the middle detector, wherein the fourth detector is configured to emit a first signal upon detecting an energetic electron, and a second signal different from the first signal upon detecting an energetic ion.

11. The system of claim 1, further including a fourth detector positioned between the side detectors and behind the middle detector, wherein the side detectors are configured to detect a first particle type and the fourth detector is configured to detect a second particle type different from the first particle type.

12. The system of claim 1, further comprising an upper detector and a lower detector that abut at a centrally positioned midplane that is orthogonal to the side detectors and orthogonal to the front of the system, wherein the upper detector and the lower detector are both positioned between the side detectors and behind the middle detector, wherein the upper detector and the lower detector are configured to emit respective signals upon detecting particles from the radioactive source, and wherein the processor is further configured to compare detection data from the upper detector with detection data from the lower detector and thereby determine whether the source is above the midplane, below the midplane, or substantially on the midplane.

13. The system of claim 1, wherein each side detector comprises an upper side portion and a lower side portion, wherein each respective upper side portion and lower side portion abut at a centrally positioned midplane that is orthogonal to the side detectors and orthogonal to the front of the system, and wherein the processor is further configured to compare signals from the respective upper side portions and lower side portions, and thereby determine whether the source is above the midplane, below the midplane, or substantially on the midplane.

14. The system of claim 1, wherein the front surface of each respective side detector is beveled at an angle of 30 degrees to 60 degrees relative to the aiming plane.

15. The system of claim 1, mounted in a pedestrian passageway and configured to measure the position and velocity and travel direction of a radioactive source in the passageway.

16. The system of claim 1, further comprising two handles mounted on orthogonal surfaces of the system and two displays mounted on orthogonal surfaces of the system, each display being configured to show a directional icon pointing toward the calculated source location.

17. The system of claim 1, further including a sound generator configured to produce a first sound when the angle of the source is positive, and to produce a second sound different from the first sound when the angle of the source is negative, and to produce a third sound different from the first and second sounds when the source is substantially aligned with the aiming plane.

18. The system of claim 1, further comprising a wearable monitor configured to transmit an alarm when a person wearing the wearable monitor has fallen down.

19. The system of claim 1, wherein the processor is further configured to generate an estimate of the source angle based at least in part upon the side detector signals, the middle detector signals, and a predetermined angular correlation function.

20. The system of claim 1, further comprising non-transient computer-readable media containing instructions which, when executed by a computer, perform a process comprising:
measuring detection rates of the side detectors and of the middle detector, respectively;
calculating a differential equal to the difference between the detection rates of the two side detectors;
dividing the differential by the middle detector detection rate, thereby obtaining a ratio;
comparing the ratio to a predetermined angular correlation function that relates particle detection rates to particle directions; and
determining, from the comparing, the sign and magnitude of the source angle.

* * * * *